United States Patent [19]

Kelly

[11] Patent Number: 5,539,971

[45] Date of Patent: Jul. 30, 1996

[54] METHOD OF MANUFACTURING AN ENDOSCOPE

[75] Inventor: Eugene J. Kelly, Bayville, N.Y.

[73] Assignee: United States Surgical Corporation, Norwalk, Conn.

[21] Appl. No.: 120,887

[22] Filed: Sep. 13, 1993

[51] Int. Cl.$^6$ ..................................................... B29D 11/00
[52] U.S. Cl. ............................... 29/418; 29/458; 264/1.1; 264/1.7; 264/129; 264/152; 264/328.8; 427/162
[58] Field of Search ........................... 264/1.1, 152, 129, 264/1.7, 1.9, 328.8; 29/418, 458; 427/162

[56] References Cited

U.S. PATENT DOCUMENTS

| | | |
|---|---|---|
| 3,089,484 | 5/1963 | Hett . |
| 3,257,902 | 6/1966 | Hopkins . |
| 3,297,022 | 1/1967 | Wallace . |
| 3,556,085 | 1/1971 | Takahashi . |
| 4,025,155 | 5/1977 | Imai . |
| 4,036,218 | 7/1977 | Yamashita et al. . |
| 4,148,550 | 4/1979 | MacAnally . |
| 4,148,551 | 4/1979 | MacAnally . |
| 4,168,882 | 9/1979 | Hopkins . |
| 4,267,828 | 5/1981 | Matsuo . |
| 4,273,110 | 6/1981 | Groux . |
| 4,300,812 | 11/1981 | Nakahashi . |
| 4,354,730 | 10/1982 | Bel . |
| 4,385,810 | 5/1983 | Hamou . |
| 4,545,652 | 10/1985 | Hoogland . |
| 4,575,195 | 3/1986 | Hoogland . |
| 4,664,486 | 5/1987 | Landre et al. . |
| 4,676,606 | 6/1987 | Takahashi . |
| 4,693,568 | 9/1987 | Takahashi . |
| 4,704,007 | 11/1987 | Landre et al. . |
| 4,723,843 | 2/1988 | Zobel . |
| 4,784,118 | 11/1988 | Fantone et al. . |
| 4,919,112 | 4/1990 | Siegmund . |
| 4,946,267 | 8/1990 | Hoogland . |
| 4,964,710 | 10/1990 | Leiner . |
| 4,993,817 | 2/1991 | Hoogland . |
| 5,005,960 | 4/1991 | Heimbeck . |
| 5,020,893 | 6/1991 | Karst et al. . |
| 5,159,753 | 11/1992 | Torrence ............................... 29/418 R |
| 5,188,092 | 2/1993 | White . |

FOREIGN PATENT DOCUMENTS

| | | |
|---|---|---|
| 3838168 | 10/1988 | Germany . |
| 3926714 | 2/1991 | Germany ................................. 29/418 |
| 544422 | 1/1977 | U.S.S.R. . |
| 686725 | 9/1979 | U.S.S.R. . |
| 683721 | 9/1979 | U.S.S.R. . |

OTHER PUBLICATIONS

Warren J. Smith, Modern Optical Engineering, pp. 159, 160 (1966).
The Handbook of Plastic Optics, 2nd Edition, pp. 56–93 (1983).

*Primary Examiner*—Mathieu D. Vargot

[57] ABSTRACT

An optical system to be incorporated in endoscopic instrumentation is provided. The optical system includes objective lens, relay lens and eye lens assemblies. The relay lens assembly includes at least one relay lens module for transferring an image between successive image planes. The relay lens module consists of two identical optical components in symmetrical arrangement relative to a center plane of symmetry. Each optical component includes a single curved lens and a doublet lens. In a preferred embodiment, the single and doublet lenses are thin lenses and are fabricated from polymeric materials. An illumination system is also provided and preferably includes a plurality of small diameter polymeric fibers in cooperation with a heat absorbing filter means.

12 Claims, 25 Drawing Sheets

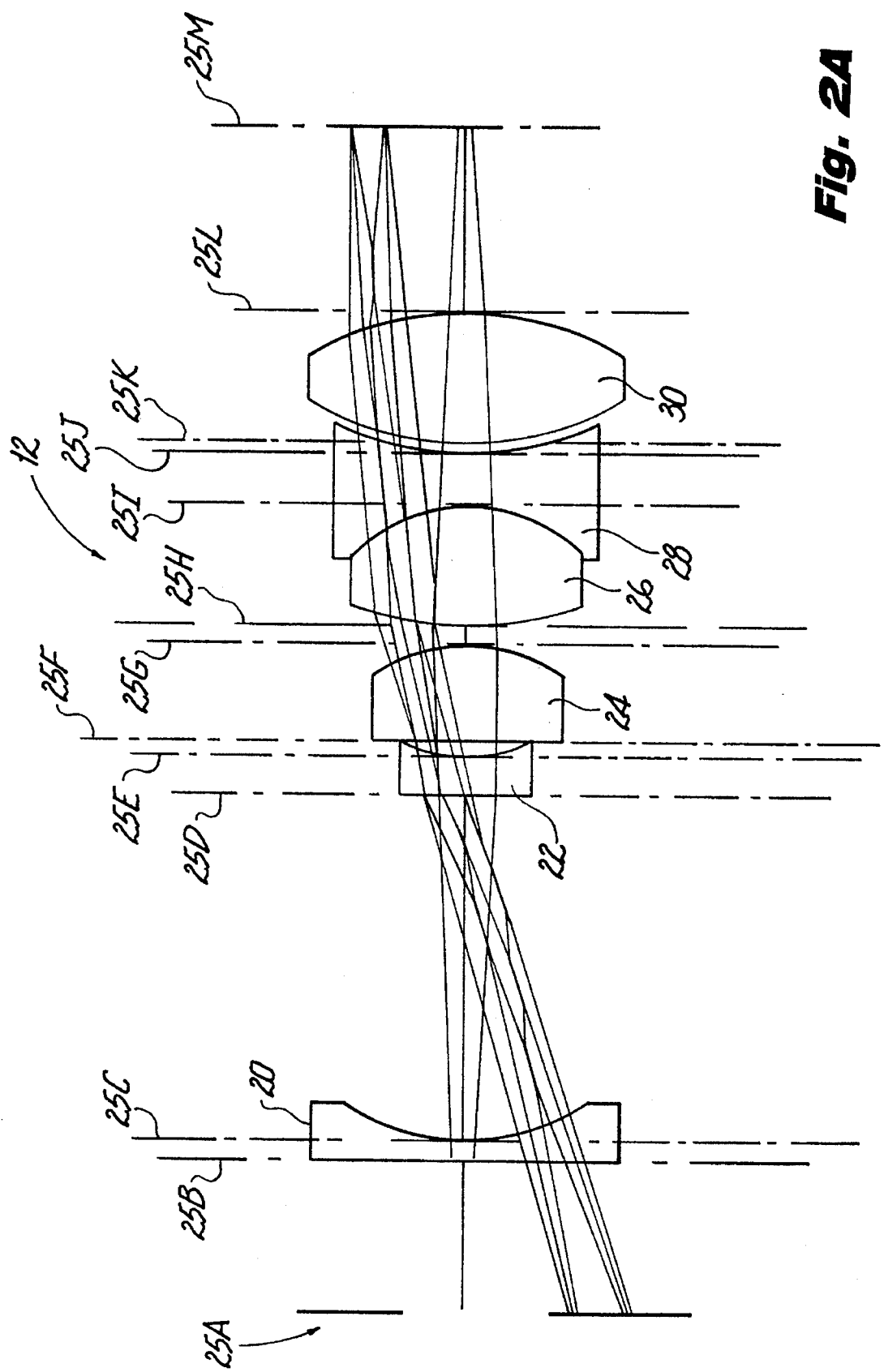

 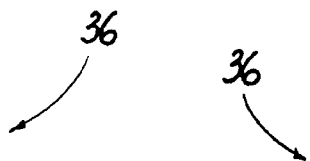 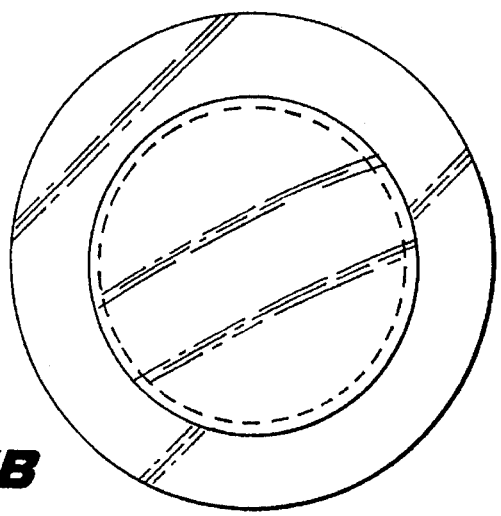
Fig. 5A
Fig. 5B
 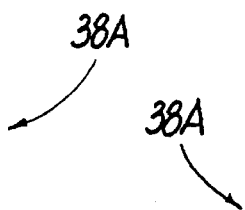 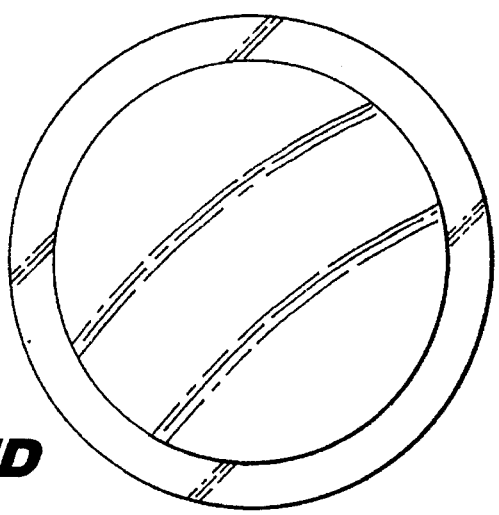
Fig. 5C
Fig. 5D
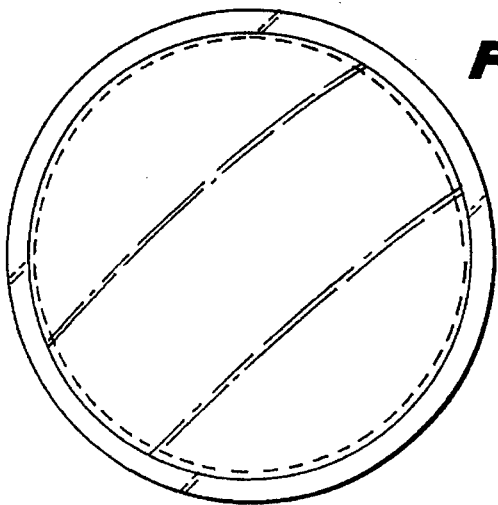 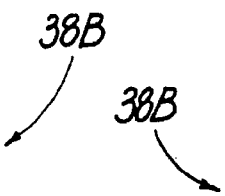 
Fig. 5E
Fig. 5F

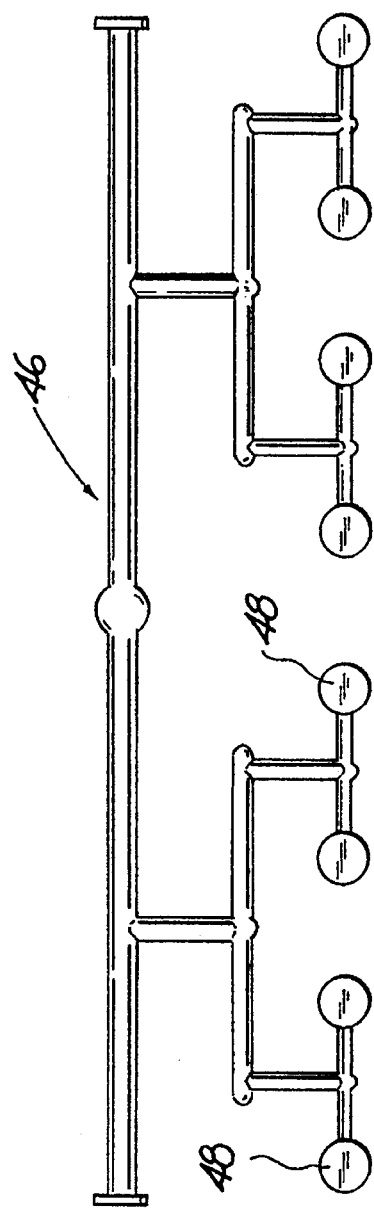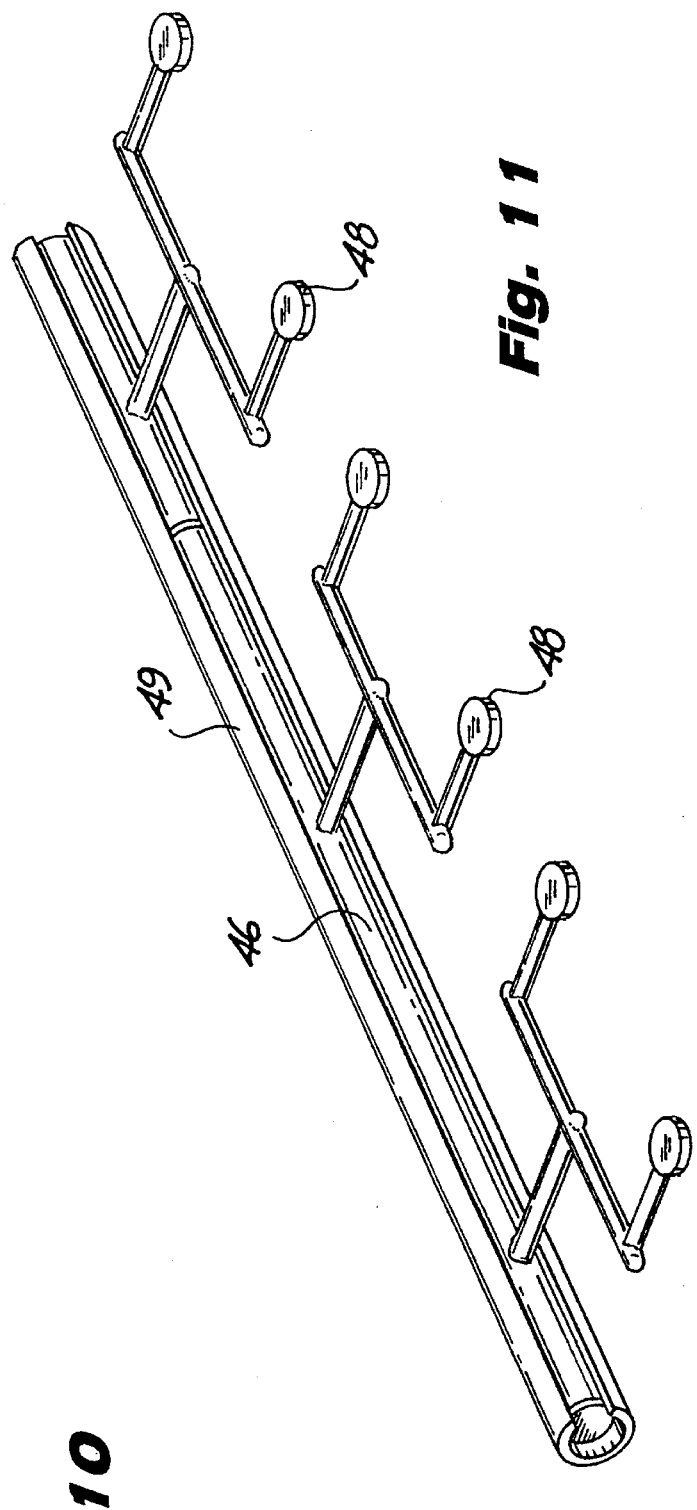

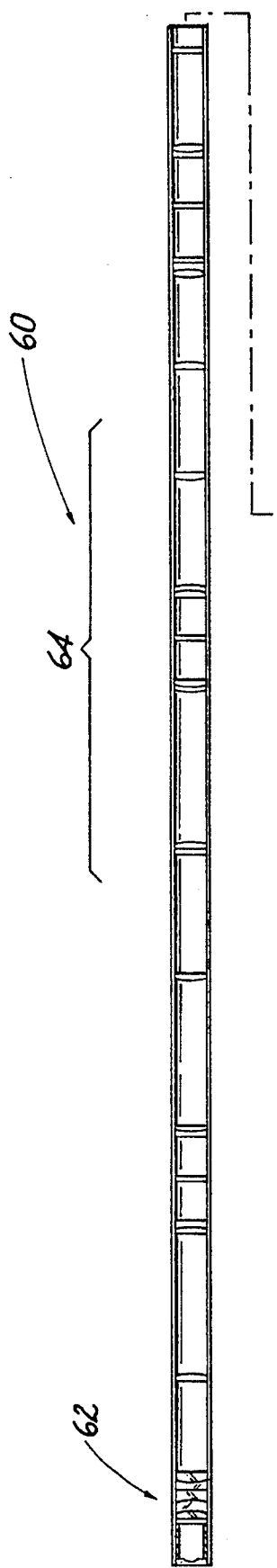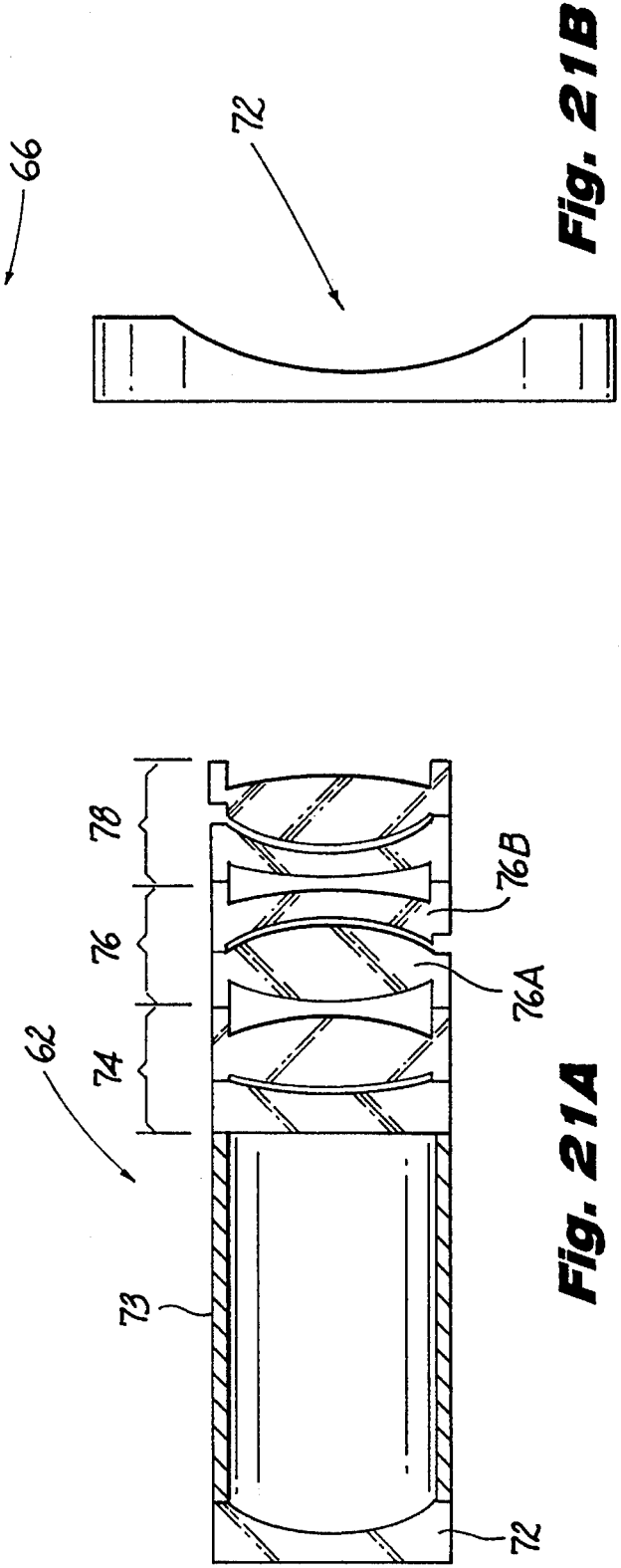
Fig. 20
Fig. 21B
Fig. 21A

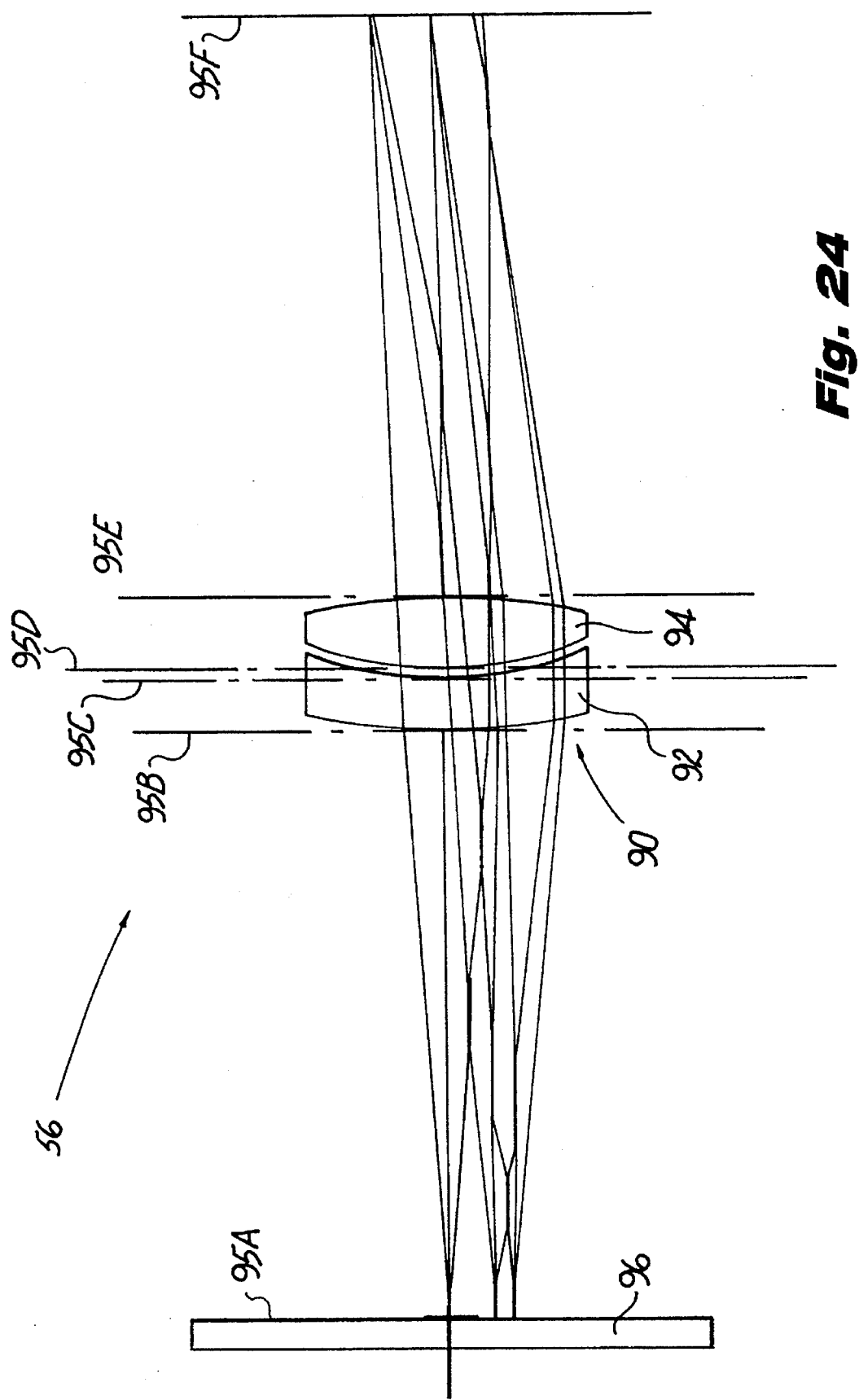

METHOD OF MANUFACTURING AN ENDOSCOPE

I. BACKGROUND OF THE INVENTION

1. Field of the Invention

This invention relates to image transmitting optical systems and, more particularly, to image transmitting optical systems for rigid endoscopes and the like in which an image of an object is transmitted through a plurality of polymeric relay lenses.

2. Description of the Related Art

Endoscopic image transmitting optical systems are extensively used to permit visualization of typically inaccessible areas within a patient's body. These systems generally include a housing enclosing a lens portion for focusing and relaying an image, and an illumination means for illuminating the region to be viewed. The lens portion used for focusing and relaying the images has typically been formed using a plurality of precision made glass lenses making up an objective portion, a relay portion and an ocular portion.

Conventional glass image transmitting optical systems have made considerable use of rod lenses and glass plano cylinders in their relay portions. See, for example, U.S. Pat. Nos. 3,257,902 (Hopkins), 3,297,022 (Wallace), 4,036,218 (Yamashita et al.) and 4,148,550 (MacAnally). These lenses are typically arranged end to end with the refractive index of the rod lenses being greater than the medium separating them and the axial length of each of the rod lenses being greater than the axial length of the medium. By using rod lenses, the major part of the length of the optical path through the optical system is provided by the lens material and the divergence of the rays in the lenses is reduced.

One major drawback to glass lens assemblies, both thin lens and rod lens types, are their relatively high costs to manufacture and assemble. Glass lenses must be carefully and precisely ground to provide acceptable transfer optics. Also, the lens assemblies must be put together into an image transmitting optical system with great precision to insure proper spacing between the lenses. This results in an expensive and relatively delicate instrument which must be handled with great care.

A second drawback to endoscopes incorporating glass lens assemblies is that due to their relative expense, they must be reused with a number of patients. Given the risks of disease transmission, this necessitates that the endoscopes undergo severe sterilization procedures. The method currently employed to effectively sterilize the instrument is gas sterilization using ethylene oxide gas. This method is extremely slow (up to 24 hours) and must be carefully controlled. Also, the ethylene oxide gas may have a deleterious effect on any plastic parts of the endoscope which, in turn, may limit the effective life span of the instrument.

Because of the aforementioned drawbacks, effort has been focused on providing an image transmitting optical system for endoscopic use which is sufficiently simple and inexpensive to fabricate and assemble in quantity such that it can be disposed of after use. For example, U.S. Pat. No. 4,784,118 to Fantone et al. suggests an optical viewing device which uses a relay lens portion composed of a plurality of injection molded rod lenses arranged in end to end fashion. Although the use of injection molding to fabricate the rod lenses does reduce the cost of grinding the lenses from optical glass, it still requires precision molding since, in order to obtain a bright image, the polymeric lenses must be much longer than their diameter. The fabrication of such polymeric rod lenses is difficult and expensive using conventional manufacturing techniques. To overcome this problem U.S. Pat. No. 4,964,710 to Leiner discloses a hybrid glass and polymeric lens optical transmitting system wherein glass plano cylinders are disposed between molded polymeric curved surface lenses. While providing clinically acceptable results, the inclusion of glass plano cylinders continues to contribute to increased expense as well as increased weight to the assembled optical system.

Accordingly, there is a clear need in the art to provide a rigid image transmitting optical system composed exclusively of polymeric thin lenses which would provide clinically acceptable optical quality, particularly in endoscopic and/or laparoscopic procedures.

II. SUMMARY OF THE INVENTION

It is therefore a primary object of the present invention to provide an image transmitting optical system comprising polymeric thin lenses, which is simple and inexpensive to manufacture in quantity while providing acceptable optical quality.

It is another object of the present invention to provide an image transmitting optical system which avoids the use of plano cylinders in the relay optics.

A further object of the present invention is to provide an image transmitting optical system which provides better performance with fewer lenses than conventional glass systems.

Another object of the present invention is to provide a method of fabricating an image transmitting optical system without the use of plano cylinders.

It is yet another object of the present invention to provide an image transmitting optical system which substantially reduces vignetting for light beams at the edge of the field.

In one form, the present invention provides a rigid image transmitting optical system for use in endoscopic and/or laparoscopic procedures and comprises an objective portion, a relay portion, and an ocular portion, all formed of polymeric thin lenses in a defined longitudinal arrangement. The polymeric thin lenses may be coated with anti-reflection materials such as Magnesium Fluoride or so-called high efficiency multi-layer (Broad-band) anti-reflection coatings to inhibit losses and improve transmission.

The present invention also may include illumination systems such as thin glass fiber bundles, light pipes, a single large diameter fiber or small diameter fibers. A preferred novel form provides illumination by means of a plurality of small diameter polymeric fibers in cooperation with a heat absorbing filter means. This configuration provides illumination comparable to existing illumination systems but with marked reduction in cost.

A novel method of manufacturing an image transmitting optical system has also been developed and includes the steps of forming polymeric lens elements, coating the formed lens elements as needed and selectively loading the coated formed lens elements into a holder such as, for example, an endoscopic tube. This novel method allows for the efficient and expeditious forming of components into a finished image transmitting optical system.

Further features of the invention, its nature and various advantages will be more apparent from the accompanying drawings and the following detailed description of the invention.

III. BRIEF DESCRIPTION OF THE DRAWINGS

Preferred embodiments of the invention are described hereinbelow with reference to the drawings. In the drawings and the description which follows, "proximal" means the end closest to the operator and "distal" means the end furthest from the operator.

Figure 1:
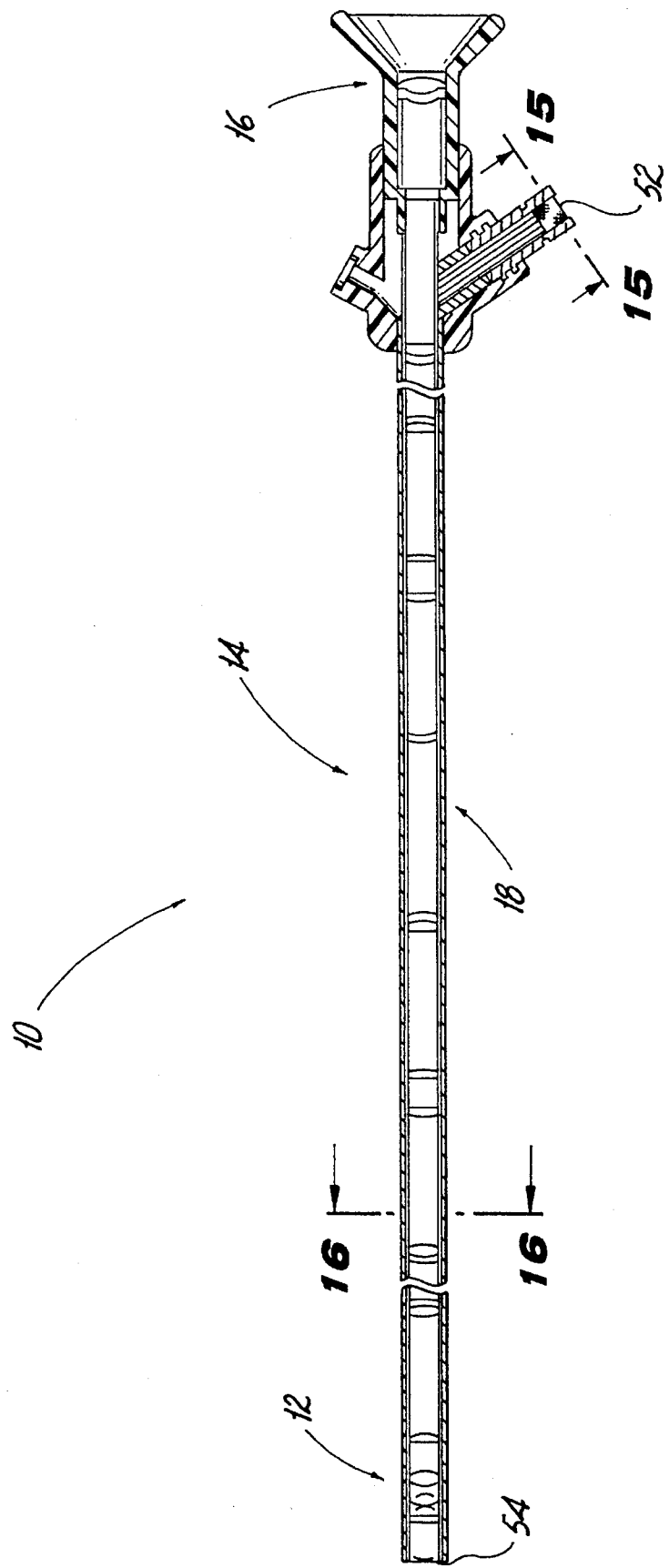
FIG. 1 is a simplified side view of an image transmitting optical system in accordance with the present invention incorporated into an endoscope.
Figure 2B:
FIG. 2A is an optical schematic of the objective portion of the optical system of FIG. 1 illustrating ray path and image orientation.
Figure 2C:
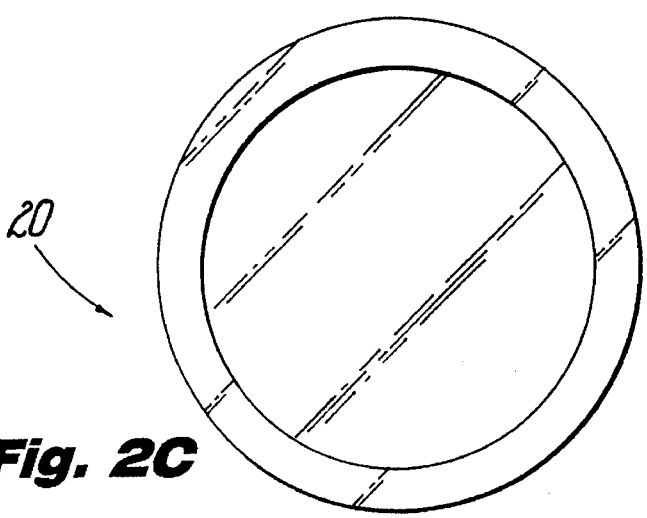
Figure 2D:
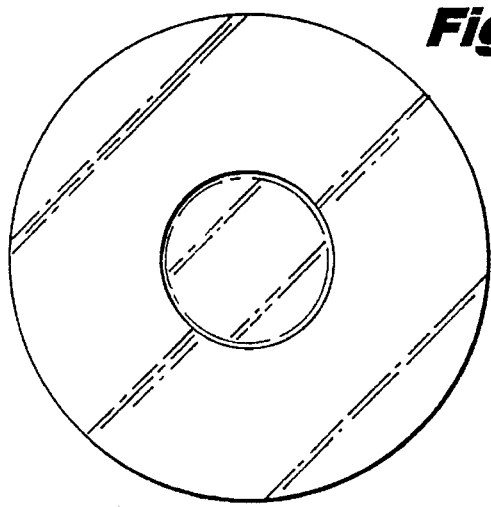
Figure 2E:
Figure 2F:
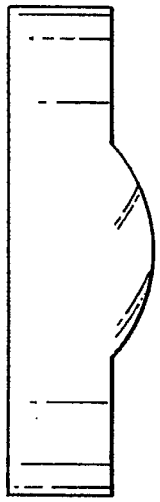
Figure 2G:
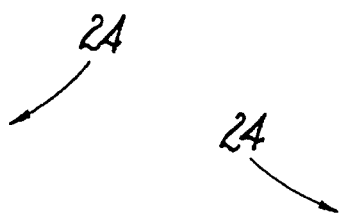
Figure 2H:
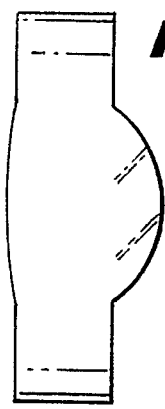
Figure 2I:
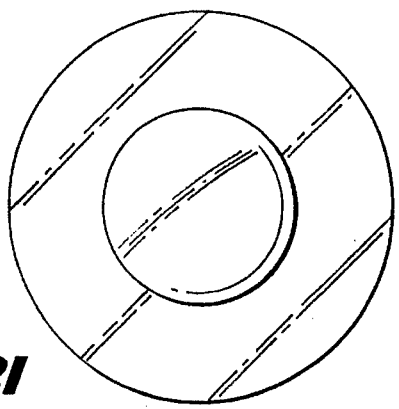
Figure 2J:
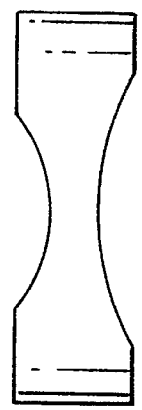
Figure 2K:
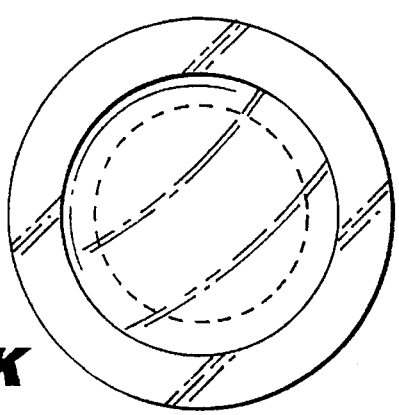
Figure 2L:
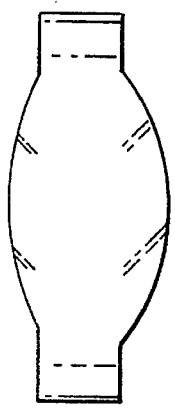
Figure 2M:
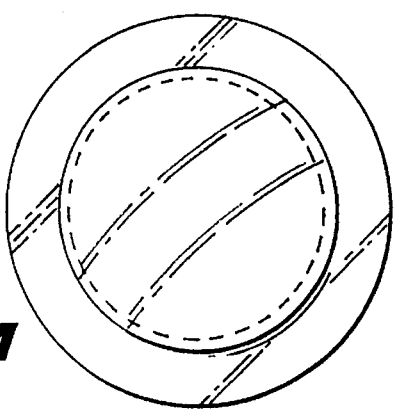
Figure 3:
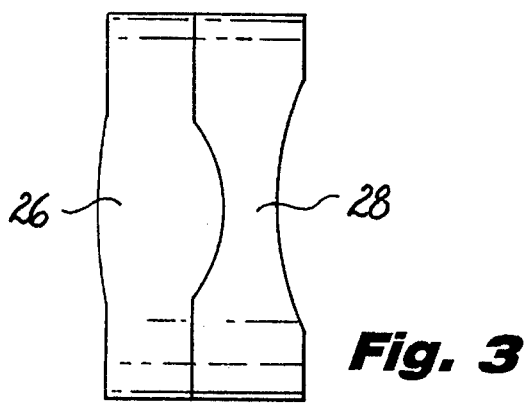
Figure 4A:
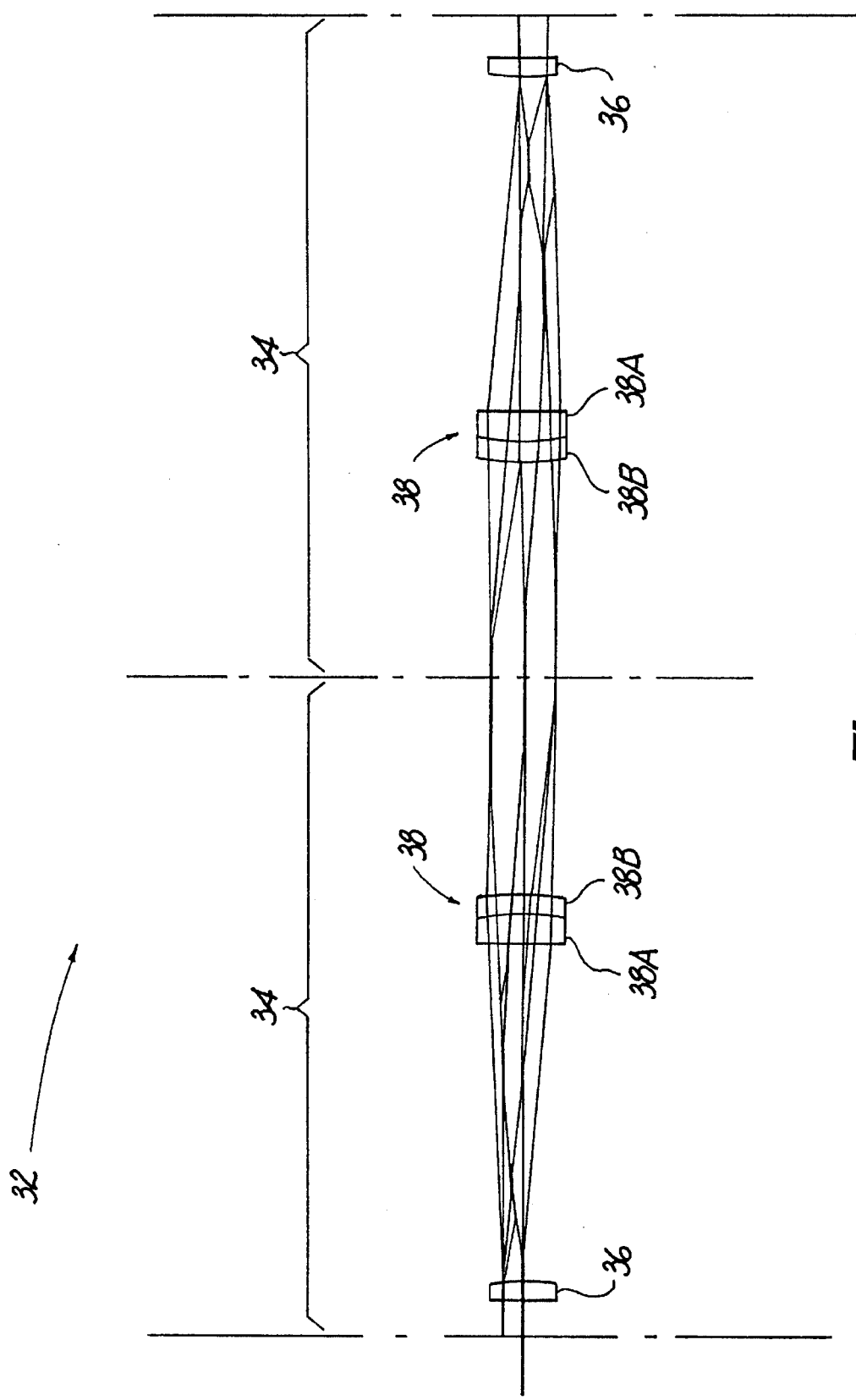
Figure 4B:
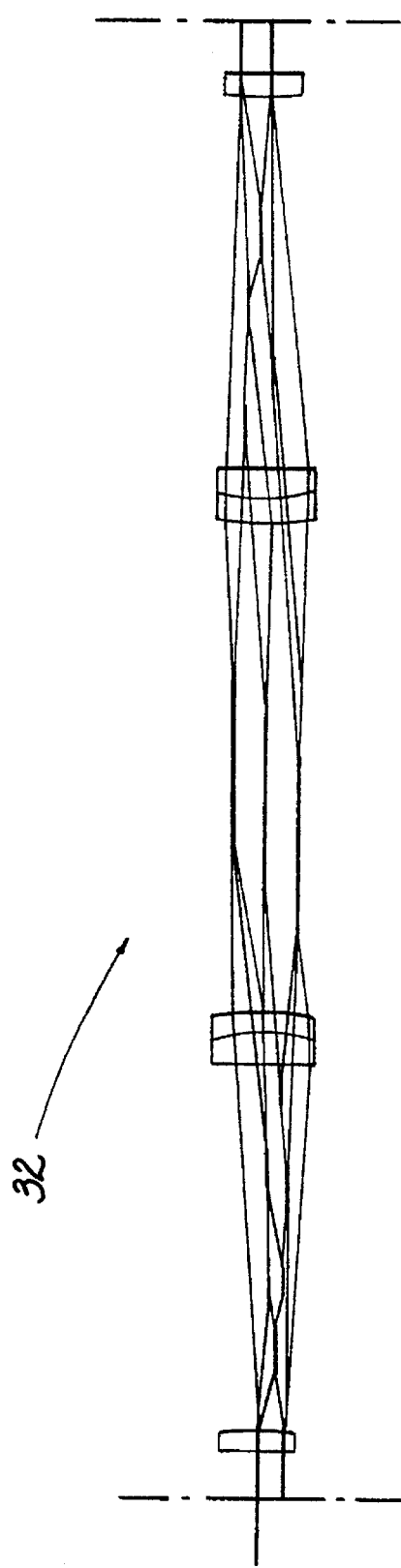
Figure 4C:
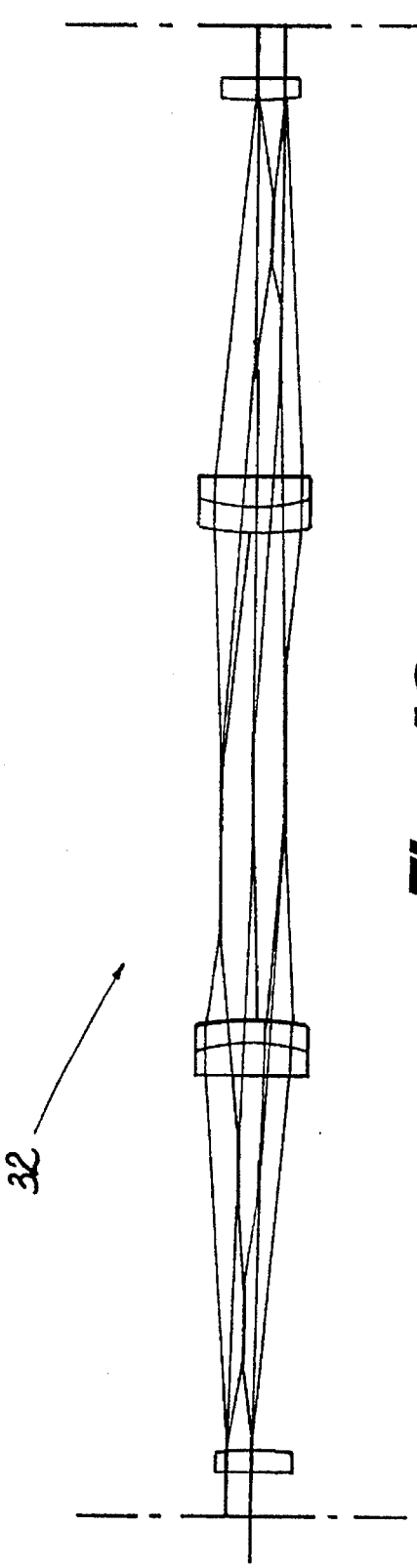
Figure 4D:
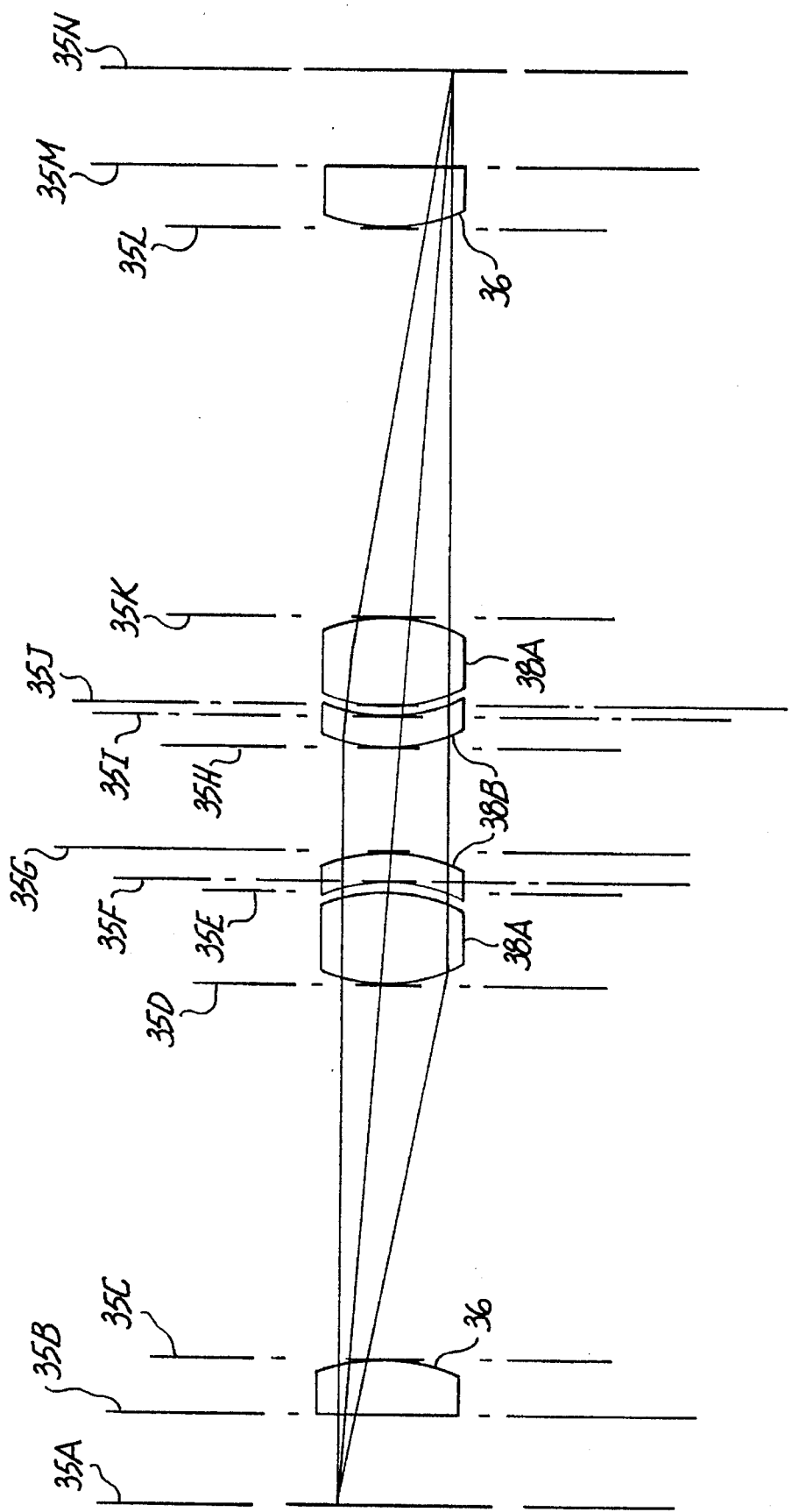
Figure 6:
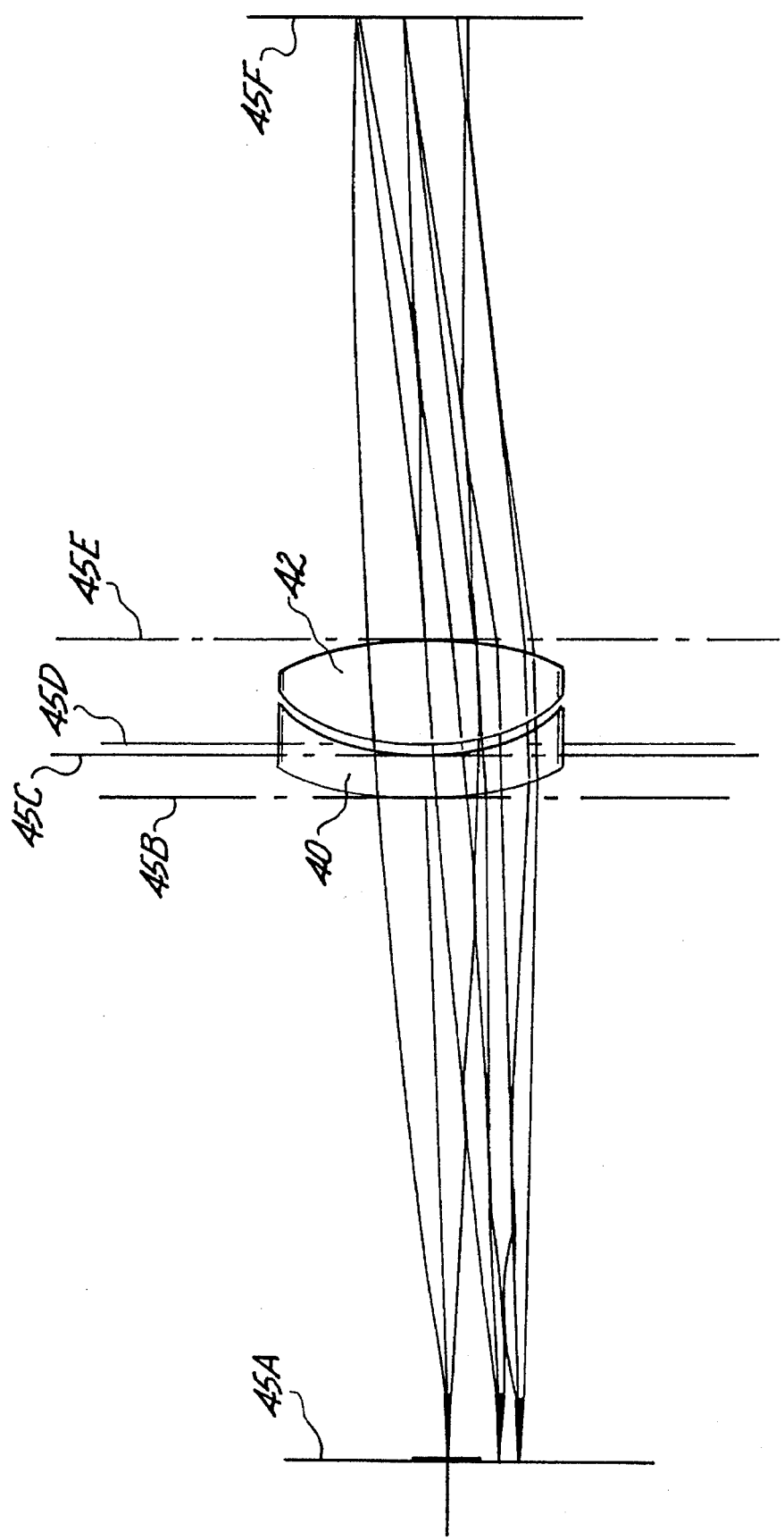
Figure 7A:
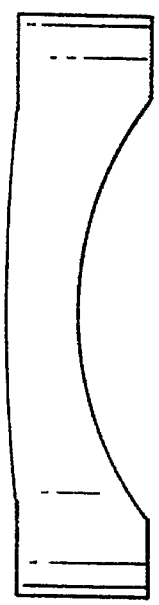
Figure 7B:
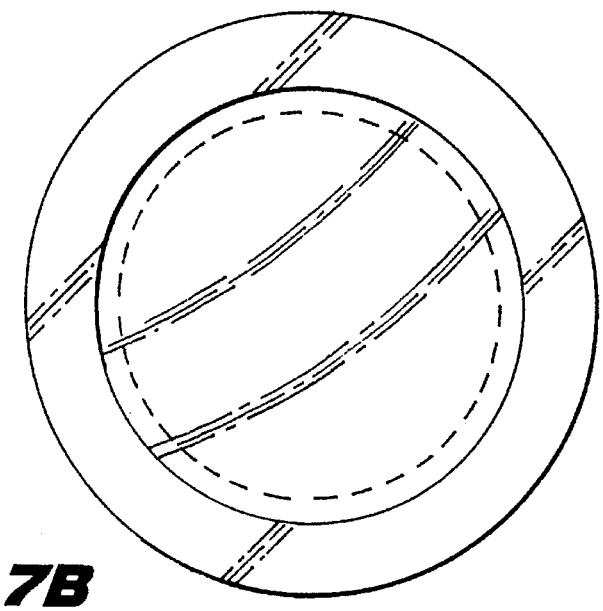
Figure 7C:
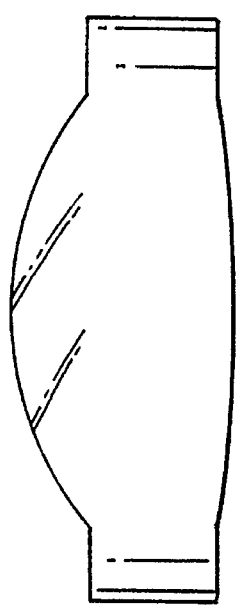
Figure 7D:
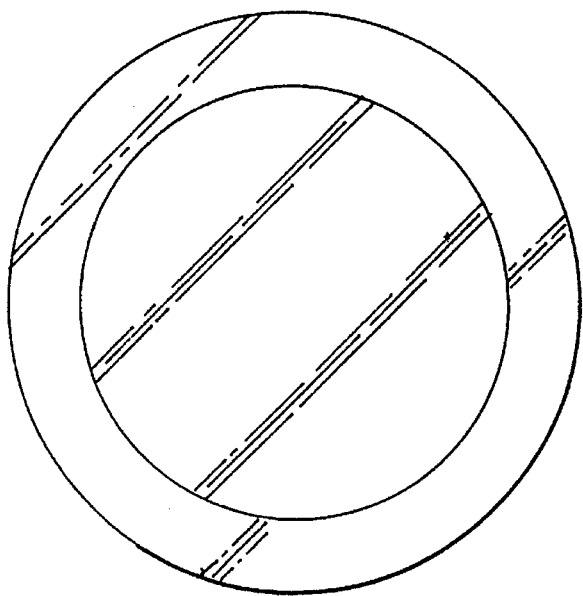
Figure 8:
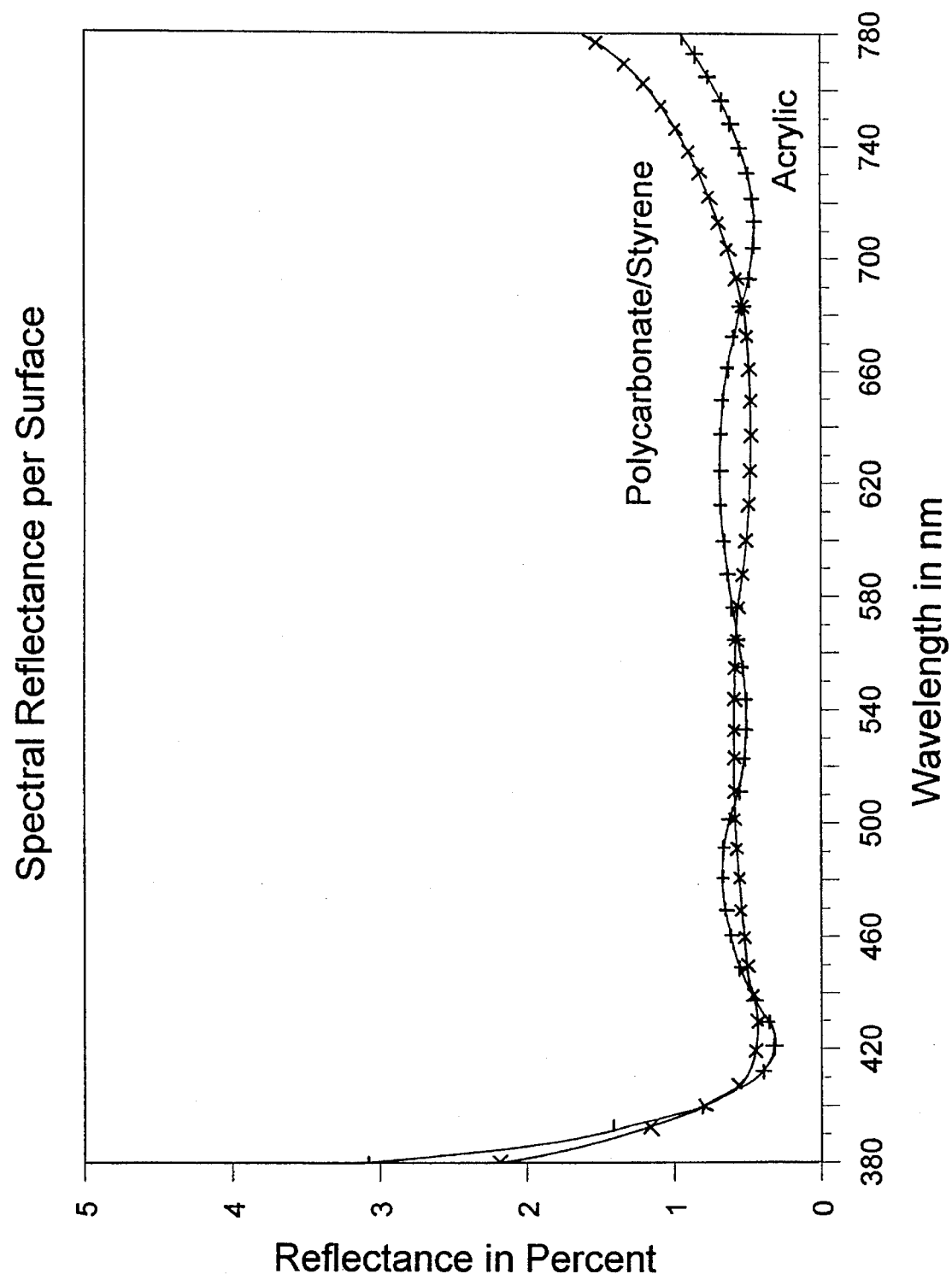
Figure 9:
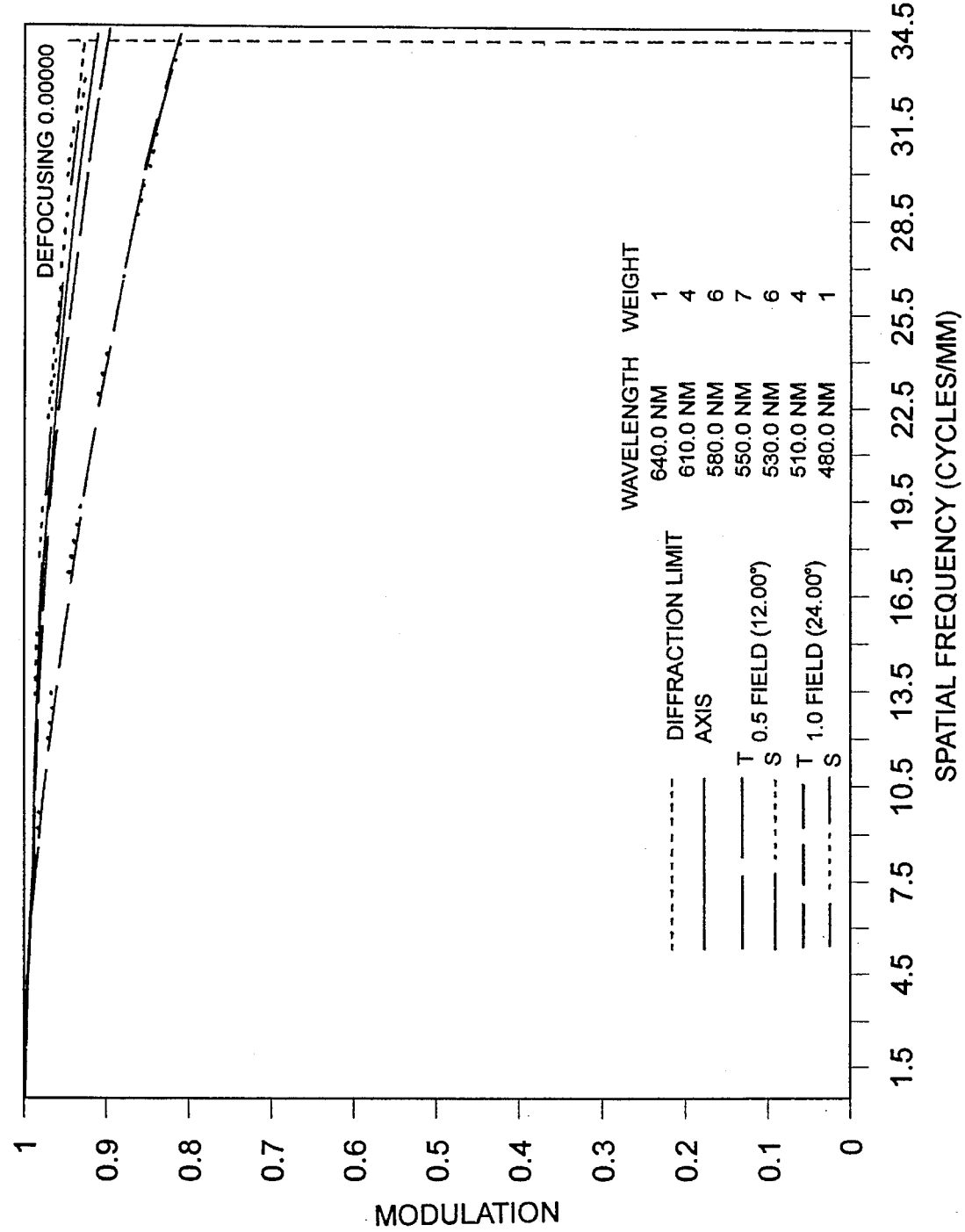
Figure 12:
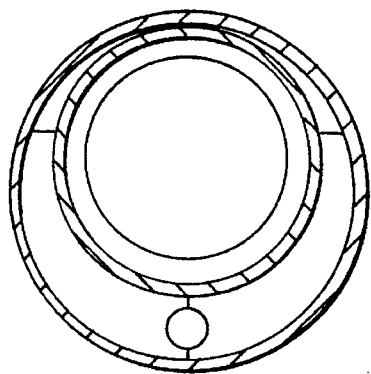
Figure 13:
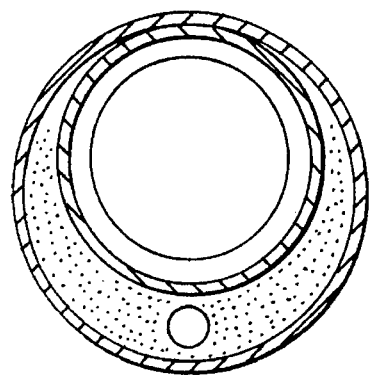
Figure 14:
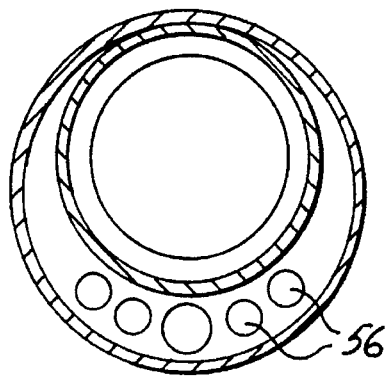
Figure 15:
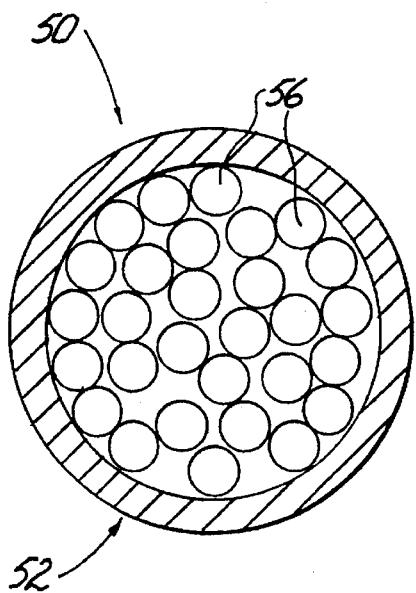
Figure 16:
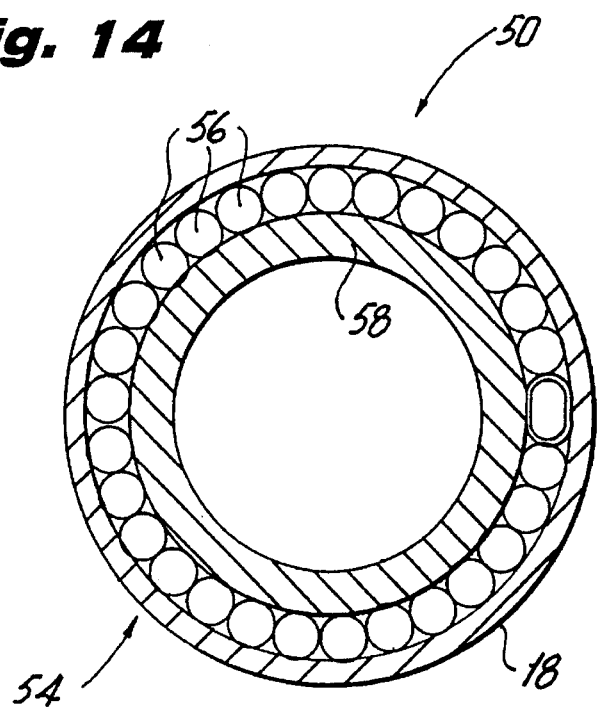
Figure 17:
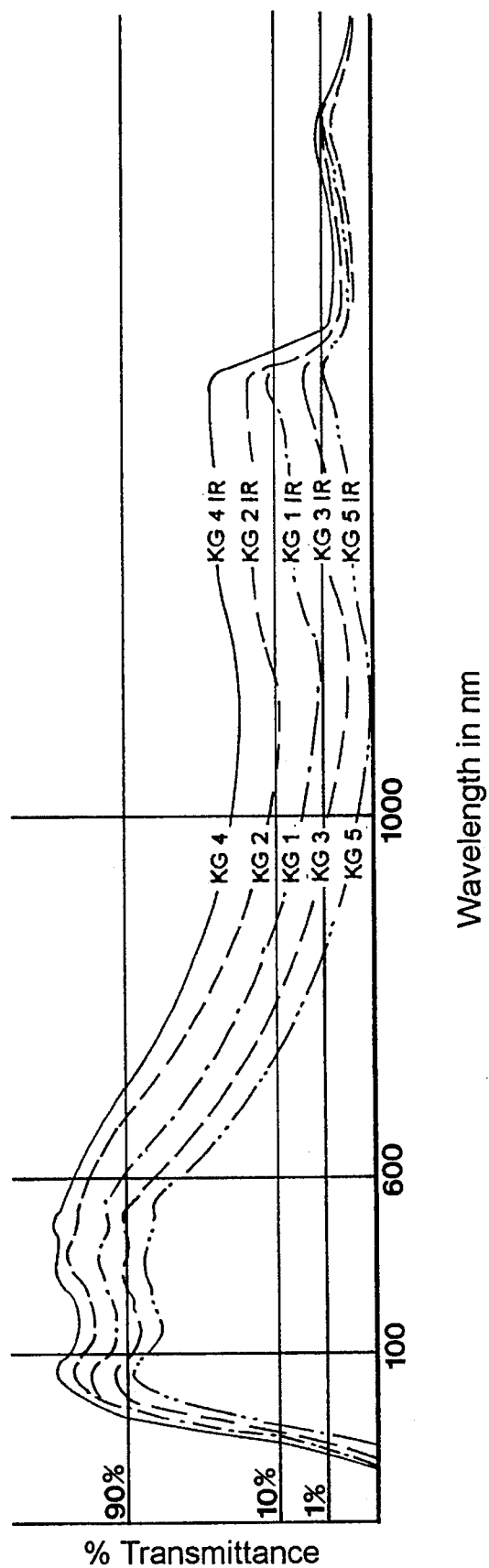
Figure 18:
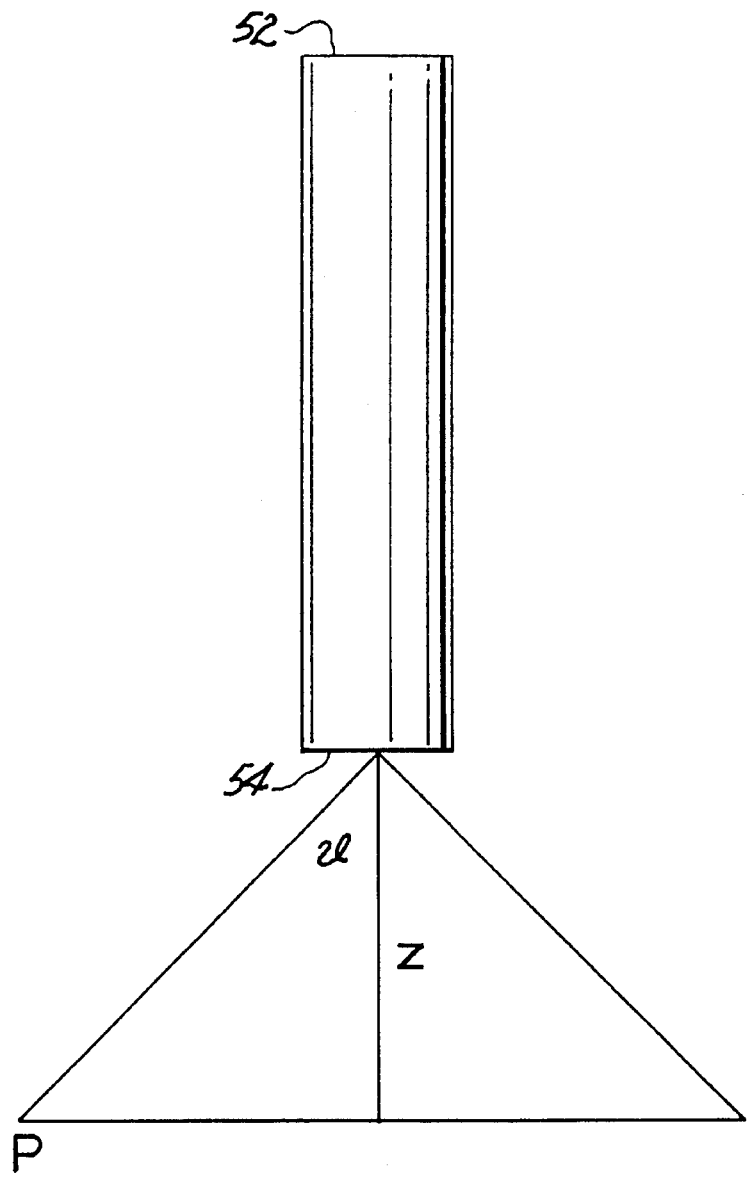
Figure 19:
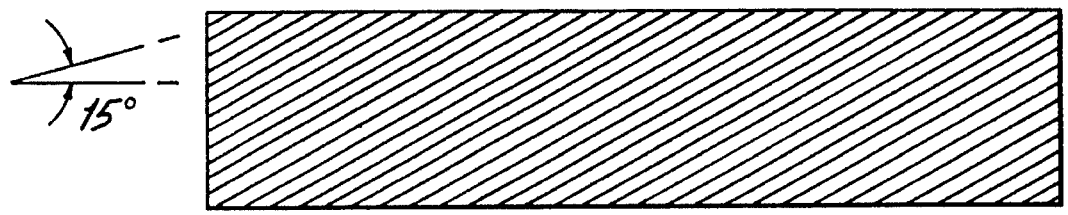
Figure 21C:
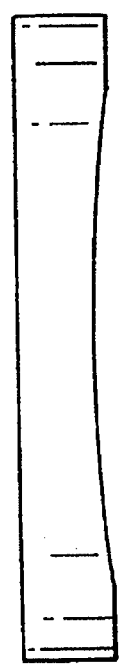
Figure 21D:
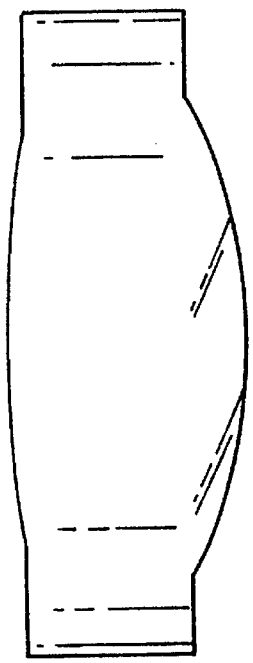
Figure 21E:
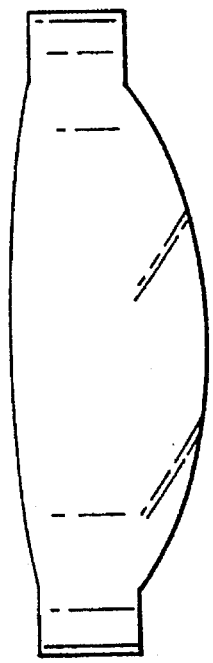
Figure 21F:
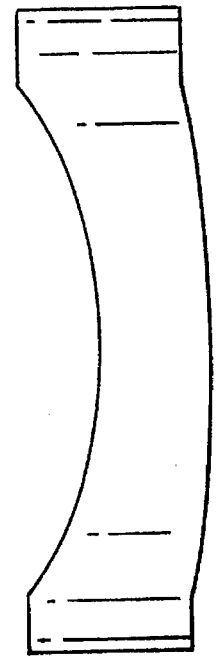
Figure 21G:
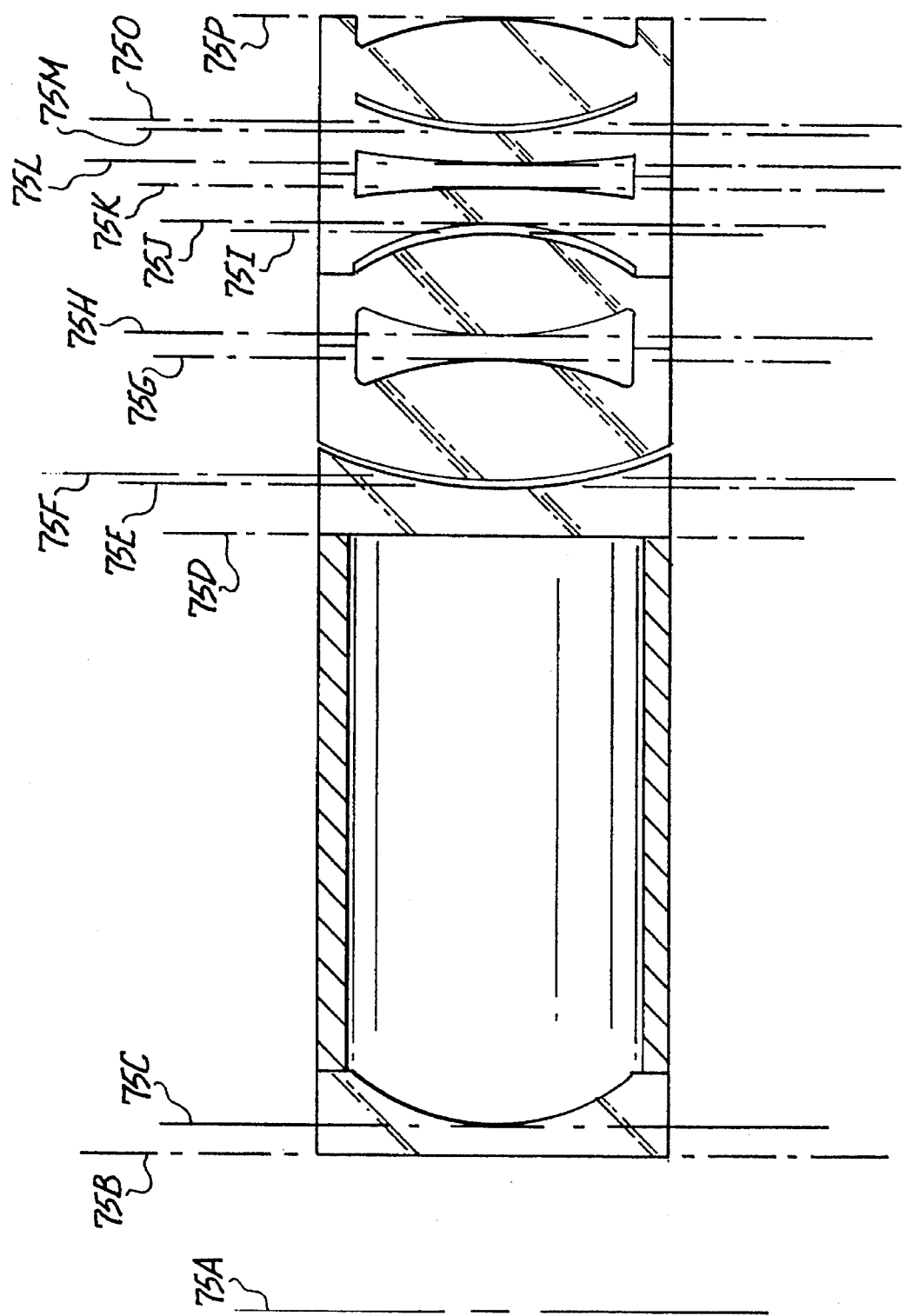
Figure 22A:
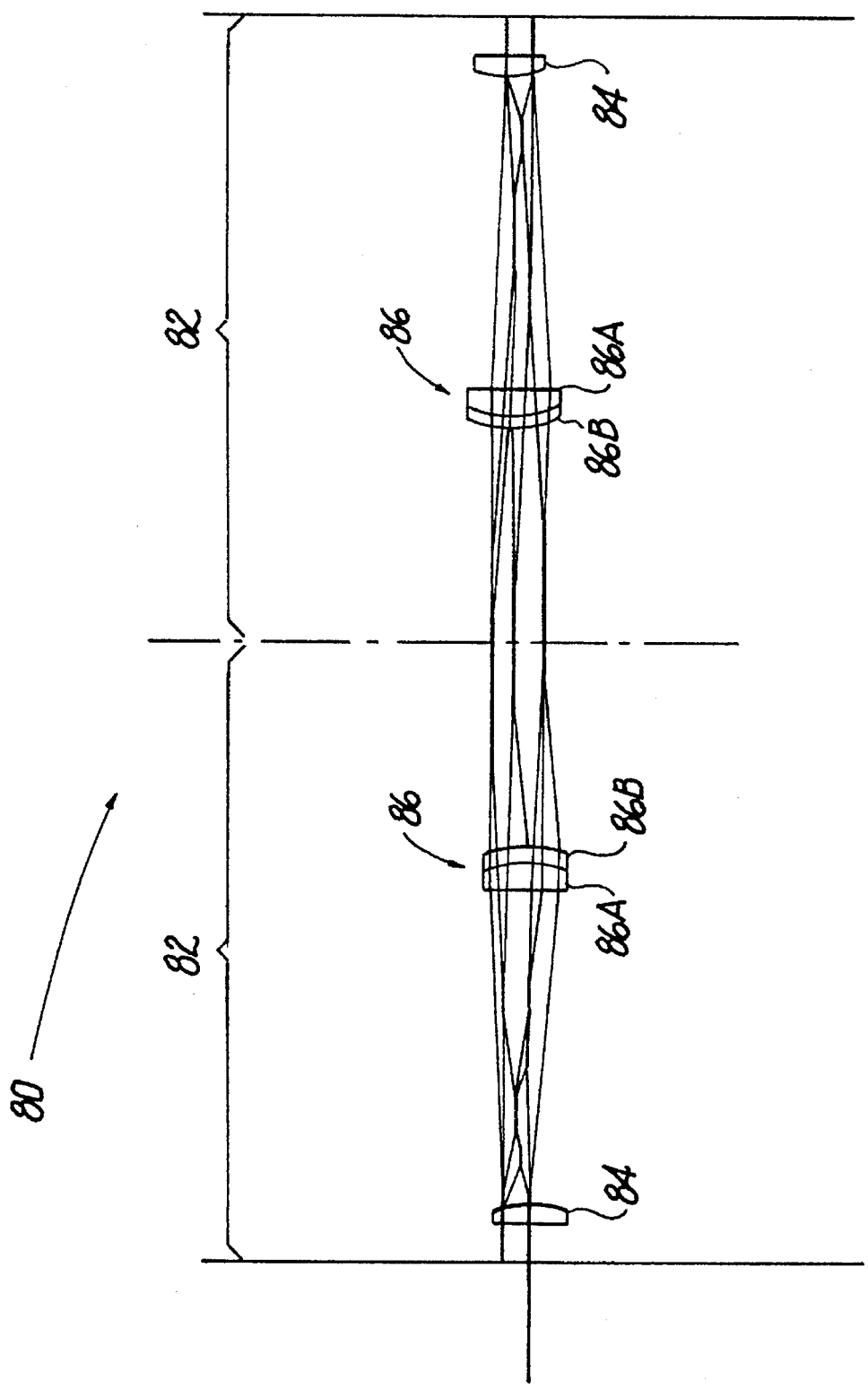
Figure 22B:
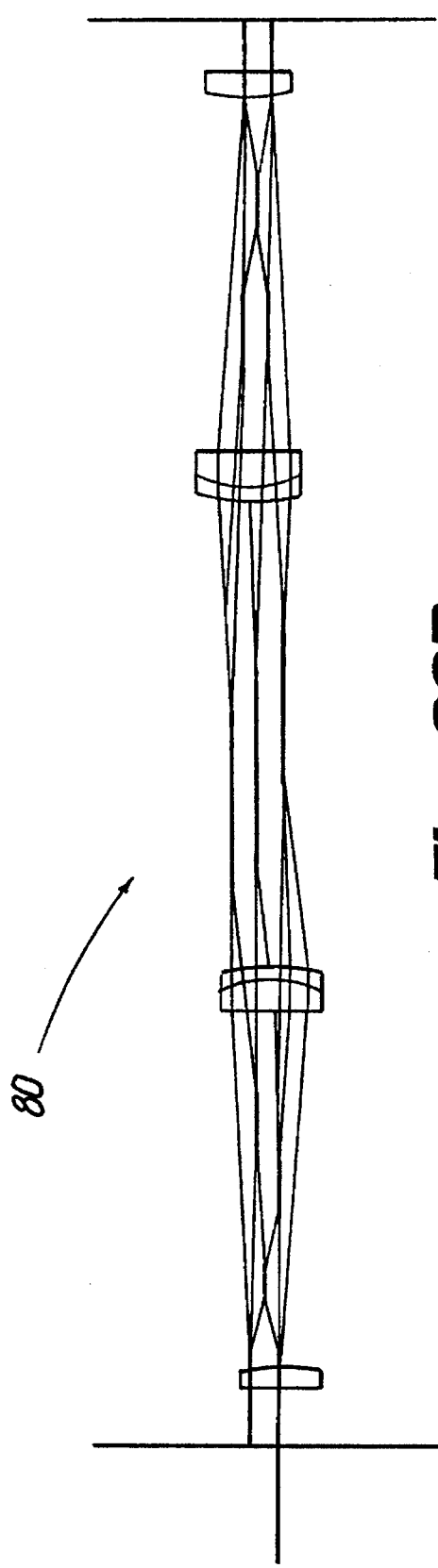
Figure 22C:
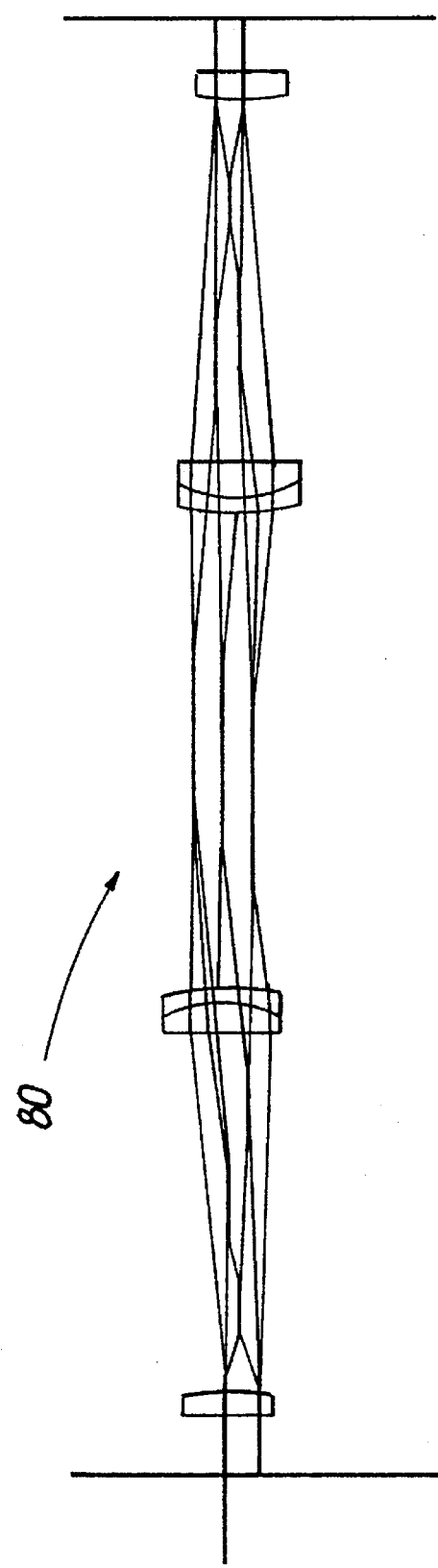
Figure 22D:
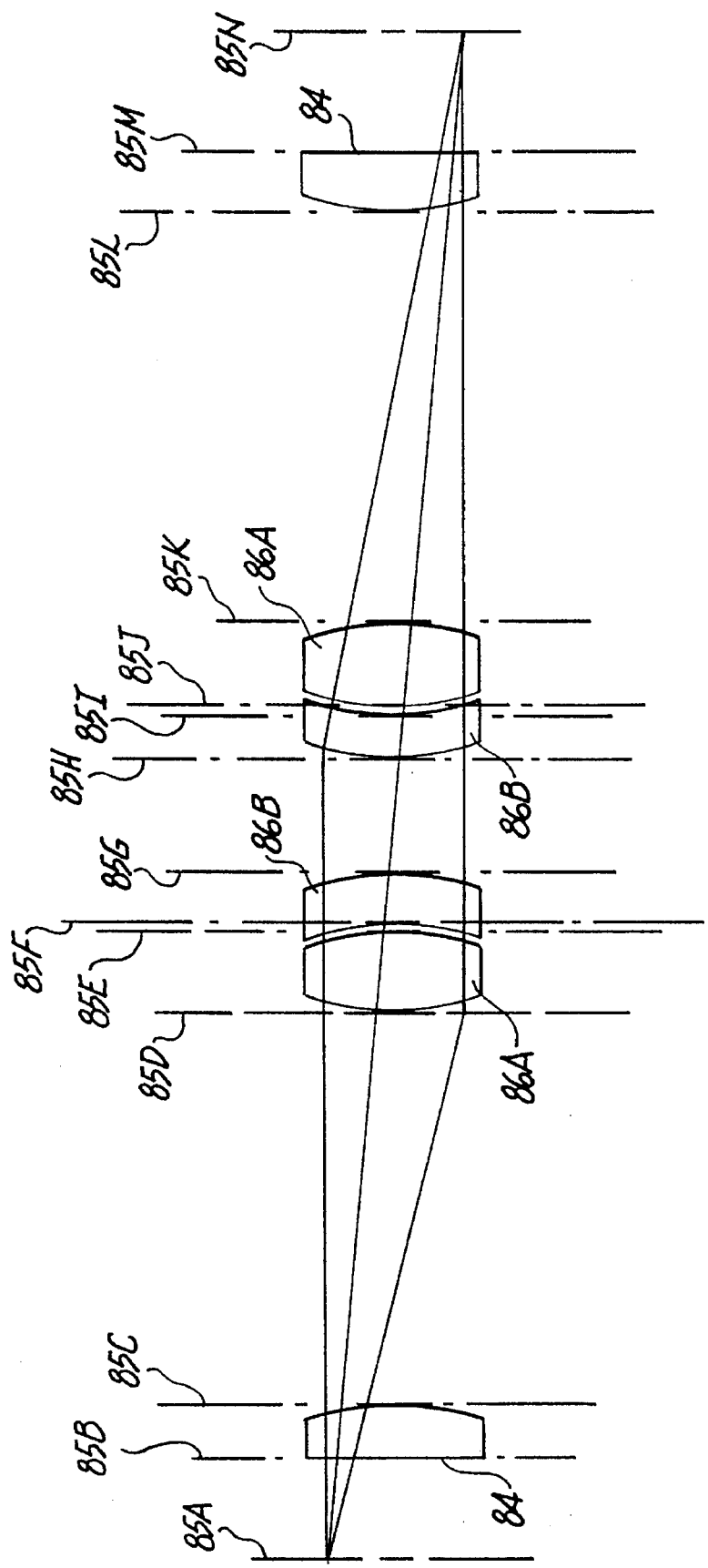
Figure 23C:
Figure 23B:
Figure 23A:
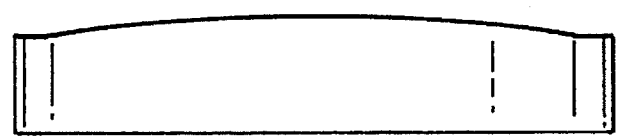
Figure 25B:
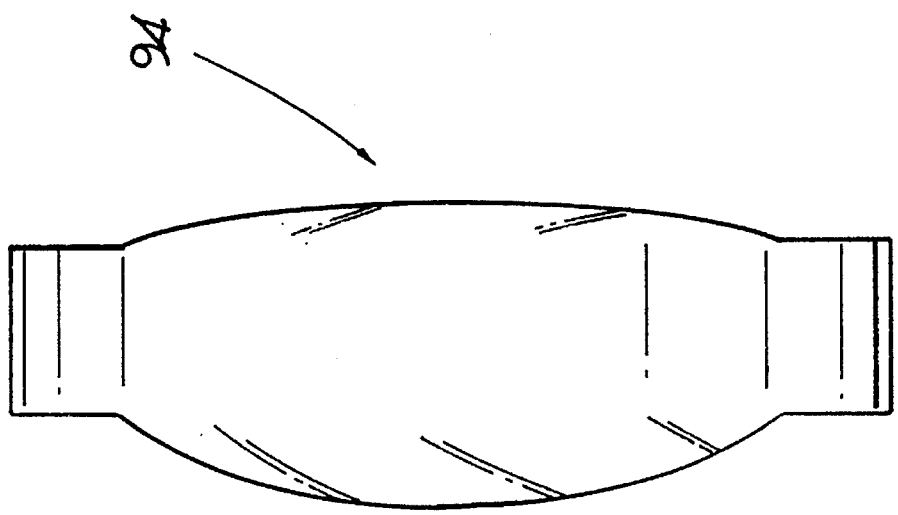
Figure 25A:
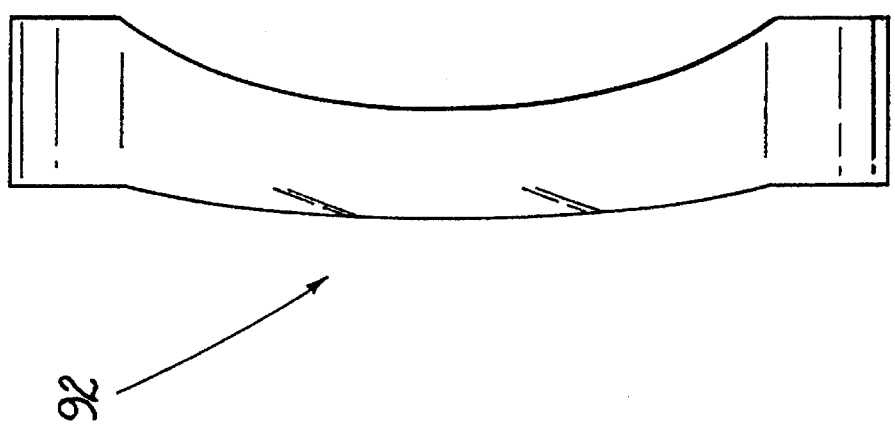

FIGS. 2B–M are side and frontal views, sequentially presented, of the lens elements, distal to proximal, of the objective portion of FIG. 2A;

FIG. 3 is a side view of the lens elements of FIGS. 2H and 2J cemented together;

FIGS. 4A–C are ray diagrams showing the relay portion of the image transmitting optical system of FIG. 1;

FIG. 4D is an enlarged optical schematic of a lens module of the relay portion of FIGS. 4A–C, illustrating ray path and image orientation;

FIGS. 5A–F are side and frontal views, sequentially presented, of the lens elements, distal to proximal, of the relay portion of FIG. 4A;

FIG. 6 is a ray diagram showing the ocular portion of the image transmitting optical system of FIG. 1, illustrating ray path and image orientation;

FIGS. 7A–D are side and frontal views, sequentially presented, of the lens elements, distal to proximal, of the ocular portion of FIG. 6;

FIG. 8 is a graphic representation of the spectral reflectance per surface of specific polymeric lens materials and for various wavelengths;

FIG. 9 is a graphic representation of modulation transfer function (MTF) curves for the optical system of FIG. 1;

FIG. 10 is a side view of a lens mold configuration used in forming the lenses of the optical system of the present invention;

FIG. 11 is a perspective view of a vacuum coating retainer used to coat the lenses of the optical system of the present invention;

FIG. 12 is a front plan view in cross section of an image transmitting optical system of the present invention using a light pipe illumination system;

FIG. 13 is a front plan view in cross section of an image transmitting optical system of the present invention using a fiber bundle illumination system;

FIG. 14 is a front plan view in cross section of an image transmitting optical system of the present invention using an illumination system comprising a plurality of single fibers;

FIG. 15 is a front plan view in cross section taken along line 15—15 of FIG. 1 showing the input port of the polymeric fiber illumination system in accordance with the present invention;

FIG. 16 is a front plan view in cross section taken along line 16—16 of FIG. 1 showing the output port of the polymeric fiber illumination system in accordance with the present invention;

FIGS. 17 is a graphical representation of internal transmittance for several conventional heat absorbing filters which may be incorporated in the illumination system of the present invention;

FIG. 18 is a schematic view of the illumination systems of FIGS. 12–14;

FIG. 19 is a side plan view in cross section of the plastic fiber illumination system of one embodiment of the present invention showing the fiber twist;

FIG. 20 is a simplified side view of an alternative embodiment of the image transmitting optical system of FIG. 1;

FIG. 21A is an optical schematic of the objective portion of the optical system of FIG. 20;

FIGS. 21B–F are side views of the lens elements, distal to proximal, of the objective portion of FIG. 21A;

FIG. 21G is an enlarged optical schematic of the objective portion of FIG. 21A defining the object plane, lens surfaces and exit image plane;

FIGS. 22A–C are ray diagrams illustrating the relay portion of the image transmitting optical system of FIG. 20;

FIGS. 22D is an enlarged optical schematic of a lens module of the relay portion of FIGS. 22A–C, defining the entrance image plane, lens surfaces and exit image plane;

FIGS. 23A–C are side views of the lens elements, distal to proximal, of the relay portion of FIGS. 22A–D;

FIG. 24 is a ray diagram showing the ocular portion of the image transmitting optical system of FIG. 20; and FIGS. 25A–B are side views of the lens elements, distal to proximal, of the ocular portion of FIG. 24.

DETAILED DESCRIPTION OF THE PREFERRED EMBODIMENTS

Referring now to the drawings and, in particular, to FIG. 1, there is shown a simplified view of the image transmitting optical system of the present invention incorporated into a conventional rigid endoscope. Optical system 10 includes an objective lens portion 12 for forming an image of an object at an entrance image plane, a relay lens portion 14 for transferring the image formed at the entrance image plane through the instrument and to an exit image plane and an ocular portion 16 for producing a magnified virtual image for the viewer. Optical system 10 also includes an illumination system for illuminating the region to be viewed. Optical system 10 finds particular application in disposable endoscopes and can be mounted within endoscopic tube 18 by conventional methods. In a preferred embodiment, endoscopic tube 18 has a working length of at least about 250 mm and a diameter of about 10.0 mm.

Referring now to FIG. 2A, the objective lens portion 12 of optical system 10 is illustrated in detail. Objective lens portion 12 includes a plurality of curved lenses 20, 22, 24, 26, 28 and 30 which are in axial alignment with each other and with the remaining components in the optical system. The objective lenses are geometrically configured to transfer an inverted image of an illuminated object from the object plane 25A to an exit image plane 25M prior to relay.

Each lens of objective portion 12 is a thin lens and is preferably fabricated from a polymeric material such as an acrylic, polystyrene, polycarbonate or copolymer styrene-acrylonitrile (SAN). The objective lenses may be formed by known injection molding techniques. Such techniques are capable of forming precise lenses relatively inexpensively and in great volume. It is to be noted that the lenses of objective portion 12 may be fabricated from other suitable materials such as glass and crystal, including materials created by SOL-GEL Technology.

In a preferred embodiment, lenses 20, 24, 26 and 30 are fabricated from an acrylic, while lenses 22 and 28 are fabricated from a polystyrene. The lens surfaces are preferably coated with a broad band anti-reflection coating to reduce reflection losses at air-lens interfaces. The geometrical characteristics of each lens in objective lens portion 12 is illustrated in further detail in FIGS. 2B–2M in which side and frontal views of the lens components are provided.

In a preferred embodiment, lenses 22–30 are configured and dimensioned such that adjacent lenses may be bonded to each other along their upper and lower surfaces. This is a significant feature in that the lenses may be secured to each other and mounted within endoscopic tube 18 as a single unit. Furthermore, this feature allows for the provision of an air gap between working surfaces of adjacent lenses.

Lens 20 may be affixed to the remaining lenses in ocular portion 12 by means of a spacer, or in the alternative may be mounted independently within endoscopic tube 18 by conventional means. It is to be noted that lens 26 may be cemented to lens 28 as shown in FIG. 3. It is also possible to affix lenses 22–30 to relay portion 14 by means of a spacer.

Referring again to FIG. 2A, the geometrical characteristics of objective portion 12 are defined by an object plane 25A, surfaces 25B–25L and exit image plane 25M. The geometrical and optical parameters of objective portion 12 are recorded in Table 1 below. In the Table, surfaces A, B–L, and M correspond to object plane 25A, surfaces 25B–25L and exit image plane 25M, respectively.

TABLE 1

| SURFACE | RADIUS | THICKNESS | MEDIUM | INDEX |
| --- | --- | --- | --- | --- |
| A | Image Plane | 1.000 E08 | Air | 1.0003 |
| B | Plano | 0.400000 | Acrylic | 1.493795 |
| C | 5.5342 | 7.001389 | Air | 1.0003 |
| D | −57.8792 | 0.800000 | Styrene | 1.595010 |
| E | 6.8701 | 0.166599 | Air | 1.0003 |
| F | 44.3554 | 2.000000 | Acrylic | 1.493795 |
| G | −3.4442 | 0.345163 | Air | 1.0003 |
| H | 7.1478 | 2.500000 | Acrylic | 1.493795 |
| I | −3.1275 | 1.000000 | Styrene | 1.595010 |
| J | 5.2587 | 0.10000 0 | Air | 1.0003 |
| K | 5.2221 | 2.500000 | Acrylic | 1.493795 |
| L | −4.9251 | 3.870228 | Air | 1.0003 |
| M | Image Plane | | | | dimensions are in millimeters
Index calculated for wavelength of 546.07 nm

Objective lens portion 12 produces an inverted image of the object at image plane 25M, which image is subsequently transmitted by relay lens portion 14.

Referring to FIGS. 4A–4C, relay lens portion 14 includes a plurality of relay lens modules 32 longitudinally arranged along a common axis. Each module 32 is identical with regard to the optical components contained therein, and is capable of transferring an image from an image plane at the entrance side of the module to a successive image plane formed on the exit side.

Referring to FIGS. 4A and 4D, each module 32 include two identical components 34 arranged in a symmetrical relationship relative to a center plane of symmetry and separated by an air gap. Each component 34 includes single curved lens 36 and doublet 38. Lens 36 is preferably of meniscus (concavo-convex) type and is fabricated from a polystyrene. Doublet 38 includes two lenses, specifically, lens 38A and 38B. Doublet 38 is preferably fabricated from two different polymeric materials to allow for the correction of chromatic aberration within the lens system. In a preferred embodiment, lens 38A is a double-convex lens and is formed from an acrylic while lens 38B is a meniscus (concavo-convex) lens and is formed from a polycarbonate. Lenses 36 and 38 may also be manufactured by known injection molding techniques. The lenses of relay portion 14 may be fabricated from other suitable materials such as glass and crystal, including materials created by SOL-GEL Technology. The lens surfaces may also be coated with a broadband anti-reflection coating to reduce reflection losses at air-lens interfaces.

FIGS. 5A–5B, 5C–5D and 5E–5F illustrate the geometrical characteristics of lens 36, 38A and 38B, respectively. In the optical arrangement of lens module 32, single lens 36 functions as a field lens, and as such, bends light ray bundles at the edge of the field, which would otherwise miss doublet lens 38 or the ocular portion 16, back toward the longitudinal axis to thereby minimize vignetting. This is a significant feature of the present invention in that the field of view may be increased without increasing the diameter of doublet 38 or the ocular lenses. It is to be noted that single lens 36 may also be displaced in the optical system from the image plane so that imperfections in lens 36 do not become visible. Further, the power of single lens 36 may be selected so that it forms an image of the object at doublet lenses 38. In this way, the entrance pupil is imaged at each of the doublet lenses 38 and the image of the object is passed through the system with reduced vignetting.

Another significant feature of the present invention is that relay lens portion 14 effectively transfers a bright image from the entrance image plane to an exit image plane without the use of glass or polymeric rod lenses. Rod lenses are typically incorporated in conventional optical systems to reduce the divergence of the light rays passing through the lenses. It is to be appreciated that the relay lens portion of the present invention consists entirely of thin lenses which may be geometrically configured and strategically positioned within the optical system to reduce the divergence of the light rays and substantially reduce vignetting of light beams at the edge of the field. In particular, in accordance with the present invention, lens separations, lens surface powers and focal lengths may be selected to substantially reduce vignetting to a value near zero. This is extremely favorable since vignetting of conventional optical systems of moderate aperture may be as high as 40% for a light beam at the edge of the field.

Referring to FIG. 4D, the geometrical characteristics of module 32 are defined by an entrance image plane 35A, surfaces 35B–33M and exit image plane 35N, respectively. The geometrical and optical parameters of the module are recorded in Table 2 below. In the Table, surfaces 35A, 35B–35M and 35N correspond to image plane A, surfaces B–M and exit image plane N, respectively.

TABLE 2

| SURFACE | RADIUS | THICKNESS | MEDIUM | INDEX |
| --- | --- | --- | --- | --- |
| A | Image Plane | 3.00000 | Air | 1.0003 |
| B | −58.7719 | 1.00000 | Styrene | 1.595010 |
| C | −25.2978 | 26.63402 | Air | 1.0003 |
| D | 36.8239 | 2.00000 | Acrylic | 1.493795 |
| E | −9.2329 | 0.10000 | Air | 1.0003 |
| F | −8.9663 | 1.00000 | Polycarb. | 1.590081 |
| G | −19.1574 | 35.91516 | Air | 1.0003 |
| H | 19.1574 | 1.00000 | Polycarb. | 1.590081 |
| I | 8.9663 | 0.10000 | Air | 1.0003 |
| J | 9.2329 | 2.00000 | Acrylic | |
| K | −36.8239 | 26.63402 | Air | 1.0003 |
| L | 25.2978 | 1.00000 | Styrene | 1.595010 |
| M | 58.7719 | 3.00000 | Air | 1.0003 |
| N | Image Plane | | | | dimensions are in millimeters

Index calculated for wavelength of 546.07 nm

In a preferred embodiment, relay lens portion 14 comprises three lens modules 32 longitudinally aligned along a common axis as shown in FIG. 1. Lens modules 32 may be interconnected by spacers. Interconnecting the modules is very desirable in that the relay lens portion may be secured as a single unit. This greatly facilitates assembly and mounting of the relay lens portion within the endoscope. As previously mentioned, it is also possible for relay lens portion 14 to be secured to objective lens portion 12 by a spacer.

The geometrical characteristics of relay portion 14 may be modified without departing from the scope of the present invention. For example, the distance between single lens 36 and doublet 38 may be varied to achieve desired optical results. It is also within the scope of the present invention for single lens 36 to be positioned adjacent doublet 38. Further, the configurations of the lenses in the relay portion may also be modified.

Referring now to FIG. 6, ocular portion 16 of optical system 10 is illustrated in detail. Ocular portion 16 includes two polymeric curved lenses 40 and 42. In a preferred embodiment, lens 40 is a meniscus lens and is fabricated from polystyrene while lens 42 is a double convex lens and is fabricated from an acrylic. It is also within the scope of the present invention to fabricate lenses 40, 42 from other suitable materials such as glass or crystal, including materials created by SOL-GEL Technology. FIGS. 7A–7B and 7C–7D illustrate the geometrical characteristics of lenses 40 and 42, respectively.

The geometrical characteristics of ocular portion 16 are defined by an entrance image plane 45A, surfaces 45B–45E and exit image plane 45F. The geometrical and optical parameters of the module are recorded in Table 3 below. In the Table, surfaces 45A, 45B–45E and 45F correspond to image plane A, surfaces B–E and exit image plane F, respectively.

TABLE 3

| SURFACE | RADIUS | THICKNESS | MEDIUM | INDEX |
|---|---|---|---|---|
| A | Image Plane | 19.188673 | Air | 1.0003 |
| B | 16.4367 | 1.000000 | Styrene | 1.595010 |
| C | 6.7967 | 0.223245 | Air | 1.0003 |
| D | 7.0497 | 3.000000 | Acrylic | 1.493795 |
| E | −17.0337 | 29.618094 | Air | 1.0003 |
| F | Exit Image Plane | | | | dimensions are in millimeters
Index calculated for wavelength of 546.07 nm

The optical system of the present invention effectively transfers a bright image of an object to the viewer without the use of glass or polymeric rod lenses. Consequently, the weight of the overall unit is reduced and the cost of manufacture is minimized. Further, proper selection of lenses and lens separations substantially reduces vignetting.

A useful parameter for determining the quality of an optical system is to calculate its image transmittance performance. Image transmittance of an optical system is affected by two factors: (a) internal transmittance of the system which accounts for material absorptions, and (b) lens surface contributions which includes reflection losses for each lens surface. FIG. 8 illustrates spectral reflectance per surface of various polymeric lens materials incorporated in the present invention. As illustrated by the graph, for wavelengths ranging from about 390 to 720 nm, the reflection of light per surface does not exceed 0.5%.

Table 4 below summarizes the transmittance characteristics of the lenses of the optical system of the present invention.

TABLE 4

| Lens | No/system | Mat. | Thickness mm | Total Thick | Tau/5 mm @ 435.8 nm | Trans |
|---|---|---|---|---|---|---|
| 20 | 1 | A | .40 | .40 | .990 | .99920 |
| 22 | 1 | S | .80 | .80 | .976 | .99617 |
| 24 | 1 | A | 2.00 | 2.00 | .990 | .99601 |
| 26 | 1 | A | 2.50 | 2.50 | .990 | .99501 |
| 28 | 1 | S | 1.00 | 1.00 | .976 | .99521 |
| 30 | 1 | A | 2.50 | 2.50 | .990 | .99501 |
| 36 | 6 | S | 1.00 | 6.00 | .976 | .97161 |
| 38A | 6 | A | 2.00 | 12.00 | .990 | .97629 |
| 38B | 6 | P | 1.00 | 6.00 | .978 | .97395 |
| 44 | 1 | S | 1.00 | 1.00 | .976 | .99521 |
| 46 | 1 | A | 3.00 | 3.00 | .990 | .99402 |

Constants

Internal transmittance per 5 mm at 435.8 nm
| | |
|---|---|
| Polycarbonate (P) | .978 |
| Acrylic (A) | .990 |
| Polystyrene (S) | .976 |

Material Absorptions

| | |
|---|---|
| Total internal transmittance at 435.8 nm is | .893 |

Surface Contributions

| | | |
|---|---|---|
| Cemented surfaces | | 1 |
| Number of AR coated surfaces | 50 | |
| Average reflection loss per surface | | .0050 |
| Average transmission per surface | | .995 |
| Total transmission due to surfaces | | .7777 |
| External transmitance | | |

.694 e = 2.718
O = objective lenses
R = relay lenses
E = ocular lenses
no/system = number of lenses in the system As depicted by Table 4, the external transmittance of the imaging system of the present invention is 0.694 (1,000 is perfect transmission). This value is comparable to conventional optical systems of the same caliber incorporating glass and aperture lenses.

A second useful parameter in evaluating the optical quality or performance is to determine the modulation transfer function (MTF) of the optical system. MTF also referred to as frequency response, sine-wave response or contrast transfer is commonly defined as the ratio of the modulation in the image to that in the object as a function of the frequency (cycles per unit length) of the sine-wave distribution pattern. A plot of modulation against frequency _(spatial frequency of the bars expressed as so many lines per millimeter in the image) is an applicable measure of the performance of an image-forming system. It should be noted that, for a given lens, the plot of MTF differs by wavelength, by field obliquity, by orientation of the bars, and from point to pointn along the lens axis.

FIG. 9 is a graph depicting MTF curves for the optical system of the present invention. MTF values were calculated along the lens axis and for points 12 degrees and 24 degrees off the axis. As illustrated in the graph, the optical system has high modulation at the low frequencies as well as at the higher frequencies for these points. Specifically, the modulation for the spatial frequency ranging from 0 cycles/mm to 34.50 cycles/mm remains above 0.90 for points along the lens axis and for points 12 degrees off axis. For points 24 degrees off axis and in the above range of spatial frequencies, modulation remains above 0.80. These modulation values are favorable when compared to conventional glass lens optical system and indicate that the optical system will be effective in producing crisp high contrast images.

Referring to FIGS. 10 and 11, the present invention also provides a novel method for manufacturing and assembling the lens components of the optical system. The method incorporates injection molding techniques, such techniques being advantageous because of their rate of production and their ability to simultaneous mold several lens components. In accordance with the method, a lens mold 46 is provided and possesses the configuration as shown in FIG. 10. Liquified polymeric material is injected into the lens mold to form the lenses in lens compartments 48 and to form the molded spine which assumes the shape of lens mold 46. The spine along with the integrally formed lenses are transferred to a coating process wherein the lens surfaces are coated with an anti-reflection coating. During this step of the procedure, the spine may be mounted within coating retainer 49 of the type illustrated in FIG. 11. Thereafter, the spine along with the attached lens components is transferred to an assembly process wherein the lenses are selectively mounted within an endoscopic tube by conventional means and the molded spine is detached from the lenses.

The novel method of the present invention allows for the efficient and expeditious forming and positioning of components into a finished image transmitting optical system. In particular, the formed spine facilitates handling and transfer of the optical components during manufacture and assembly. Further, lens mold 46 may be dimensioned and configured such that the molded lenses are at desired positions relative to each other. For example, a lens mold for the relay portion of the optical system may include six single lens mold compartments 48 which correspond with the six single lenses incorporated in the relay portion. The lens compartments may be longitudinally positioned such that they correspond to the positioning of the single lenses in the endoscope. This will greatly facilitate assembly because the single lenses will already be at their intended positions when mounted within the endoscopic tube.

It is also within the scope of the present invention to incorporate an illumination system for illuminating the distal region to be viewed. Any conventional illumination system may be used including a light pipe as depicted in cross-section in FIG. 12 and systems incorporating fiber optic technology as illustrated in FIGS. 13 and 14.

In order to meet design and cost objectives of the optical system of the present invention, the illumination system preferably incorporates fiber optic technology. It is also preferred that the system comprise polymeric fibers as opposed to a thin glass fiber bundle as shown in FIG. 13 which is expensive to manufacture and adds undesirable weight to the endoscope. Furthermore, the preferred illumination system includes a number of single fibers 56 as depicted in FIG. 14 and as is conventional in the art as compared to a single large-diameter fiber which typically fails to produce and convey sufficient light for the unit.

Referring back to FIG. 1, in combination with FIGS. 14–16, the preferred illumination system is illustrated. Illumination system 50 preferably consists of an input port 52 near the proximal end of the endoscope and an output port 54 at the distal end thereof. At input port 52, the polymeric fibers are formed into a bundle as shown in FIG. 15. Thereafter, the fibers traverse the length of endoscopic tube in an annular region defined between outer tube 18 and inner coaxial tube 58 as shown in FIG. 16 and terminate at output port 54. The lens elements of the optical system may be mounted within inner tube 58. In a preferred embodiment each fiber 56 has a diameter of about 1 mm and is fabricated from a polymeric material such as acrylic, coated with an outer polymeric material with a lower index of retraction such as PTFE (Teflon©, for example). Acrylic is a suitable material for each fiber 56 since it has a low absorption value, its internal transmittance (ti) is 97–98% at a wavelength of 330 nm and it is relatively inexpensive. The coating or cladding with a thin layer of PTFE reduces leakage of light from one fiber to the next and to the external surroundings of the fibers. In use, the light source is imaged on input port 52 of the system. An adapter mechanism may be used to establish communication between the light source and input port 52. The rays of light falling on fibers 56 are trapped therein by internal reflection. The light travels along the core of the fiber by repeated reflections within the fibers thereby transmitting the light to the distal or output port 54 of the endoscope and onto the object. With a clad fiber the total reflection takes place at the interface between the core and the cladding and is thus unaffected by minor imperfections on the outer surface of the cladding. With an unclad fiber, damage or contamination of the surface can impair the reflection and thereby drastically reduce the transmittance.

A heat absorbing or reflecting filter may be provided between the light source and input port 52 to at least partially absorb or reflect incidental electromagnetic radiation emitted from the light source and thereby preserve the integrity of the polymeric optical fibers. Suitable heat absorbing or reflecting filters for this purpose are manufactured by various suppliers of glass and special optical coatings.

FIG. 17 depicts internal spectral transmittance curves for typical heat absorbing filters manufactured by Schott Technologies. Note that the absorption of the filters increases (internal transmittance decreases) strongly for the ultraviolet region, i.e., wavelength shorter than 400 nm, and also decreases for the infrared region, i.e., wavelength greater than approximately 750 nm. Thus, a substantial portion of the heat generated by the light source is absorbed (typically about 80%). Further, as detailed by the graph, the internal transmittance remains relatively constant throughout the visible spectrum (wavelengths ranging from about 400 nm to 760 nm). This is of significant importance in the design of an endoscope, where detail of the image is often distinguished by details of color. Uniform transmittance throughout the visible spectrum is a significant parameter for producing good color.

The performance of an illumination system is controlled by the amount of light transmitted from the source and the angle of the field illuminated by the light cone emerging from the output port in the endoscope. The illuminance of the object can be calculated by the following equation:

$$I_o = I_s \times A_{op} \times T_{fb} \times \text{COS}(\_) \frac{4}{z^2}$$

wherein
  $I_o$=Illuminance of the Object
  $I_s$=Illuminance of the Source
  $A_{op}$=Area of the output port
  $T_{fb}$=transmission of the fiber
  $\_$=angular position of the object relative to the longitudinal axis of the endoscope
  z=distance from the output port to the object plane
FIG. 18 illustrates the parameters of the above equation.

Thus, in the illumination system of the present invention, assuming the illumination transmission for the acrylic fibers ranges from 60–80%, the illuminance of an object located 25 mm(z) away from the scope and at an angle 34° (_) would be as illustrated in the Table below for the following light sources:

| Luminance (× 100 stilb) | Illuminance (foot-candle) |
|---|---|
| 1 | 794.14 |
| 19 (750-watt projection lamp) | 15090 |
| 55 | 50830 |
| 100 (Carbon-arc lamp) | 79414 |

The scope of the field of illumination may be increased by twisting the fibers at an angle, preferably about 15°, relative to the longitudinal axis defined by the fiber bundle, as shown in FIG. 19.

Referring now to FIG. 20, there is shown a simplified view of an alternative embodiment of the optical system of the present invention incorporated into a conventional endoscope. Optical system 60 includes objective lens portion 62, relay lens portion 64 and ocular portion 66. Each lens in optical system 60 is preferably formed from a polymeric material, although other suitable materials such as glass and crystal may be substituted therefor. Relay lens portion 64 of this embodiment utilizes the basic arrangement of lenses of the relay lens portion of the embodiment of FIG. 1, but differs from the above-described assemblies with respect to geometrical characteristics and lens materials.

Referring initially to FIG. 21A, objective lens portion 62 of optical system 60 is illustrated and includes a plurality of polymeric axially aligned lenses 72–78. Lens 72 is a single lens, preferably of plano-convex type as shown in FIG. 21B and is bonded along its convex surface to spacer 73. Lenses 74, 76 and 78 are each doublet lenses and are proximally disposed relative to lens 72 on the proximal side of spacer 73. In a preferred embodiment, lens 74 includes meniscus (concavo-convex) lens 74A and double-convex lens 74B, which are fabricated from a polystyrene and an acrylic, respectively. FIGS. 21C and 21D depict the geometrical characteristics of the lenses in doublet 74.

Doublets 76 and 78 are identical to each other and include double convex lens 76A and meniscus lens 76B. Preferably, the double convex lens is fabricated from acrylic while the meniscus lens is fabricated from polycarbonate. FIGS. 21E and 21F illustrate the geometrical characteristics of the lenses in doublet 76 and doublet 78. Each of the lenses in doublets 76 and 78 are separated by an air gap and may be secured to each other along their peripheries by conventional adhesive means. In a preferred embodiment, doublets 74, 76 and 78 are connected to each other along common end surfaces or by spacers. This is an important feature of the present invention in that the objective portion is assembled as a single unit which thereby facilitates mounting of the portion within the endoscope.

Referring to FIG. 21G, the geometrical characteristics and optical parameters of objective lens portion 62 are defined by object plane 75A, surface planes 75B–O and exit image plane 75P. The geometrical and optical parameters of objective lens portion are recorded in Table 5 below:

TABLE 5

| SURFACE | RADIUS | THICKNESS | MEDIUM | INDEX |
|---|---|---|---|---|
| A | Image Plane | 1.0000E + 08 | Air | 1.0003 |
| B | Plano | 0.400 | Acrylic | 1.493795 |
| C | 3.1554 | 6.463 | Air | 1.0003 |

TABLE 5-continued

| SURFACE | RADIUS | THICKNESS | MEDIUM | INDEX |
|---|---|---|---|---|
| D | 499.4400 | 0.787 | Styrene | 1.595010 |
| E | 20.0274 | 0.127 | Air | 1.0003 |
| F | 18.7848 | 2.540 | Acrylic | 1.493795 |
| G | −6.5809 | 0.127 | Air | 1.0003 |
| H | 9.3673 | 2.540 | Acrylic | 1.493795 |
| I | −4.3228 | 0.127 | Air | 1.0003 |
| J | −4.1407 | 0.787 | Polycarb. | 1.590081 |
| K | −17.0259 | 0.254 | Air | 1.0003 |
| L | 17.0259 | 0.787 | Polycarb. | 1.590081 |
| M | 4.1407 | 0.127 | Air | 1.0003 |
| N | 4.3228 | 2.540 | Acrylic | 1.493795 |
| O | 9.3673 | 6.129 | Air | 1.0003 |
| P | Exit Image Plane | | | | dimensions are in millimeters
Index calculated for wavelength of 546.07 nm

Referring now FIGS. to 22A–22C, in combination with FIG. 20, relay lens portion 64 is illustrated in detail. Relay lens portion 64 includes a plurality of axially aligned relay lens modules 80. As best shown in FIGS. 22A and 22D, each lens module 80 possesses a pair of identical lens components 82 arranged in a symmetrical relationship relative to a center plane of symmetry. Each lens component 82 includes two lenses, namely single lens 84 and doublet 86 which may be connected along adjacent end surfaces by a spacer. Single lens 84 is preferably a meniscus (concavo-convex) lens and is fabricated from a polycarbonate. Doublet 86 consists of lens 86A which is preferably a double convex lens, and second lens 86B which is preferably a meniscus (concavo-convex) lens. In a preferred embodiment, lens 86A is formed from acrylic while lens 86B is formed from polystyrene. Relay lens portion 64 as well as objective portion 62 are not limited to lenses fabricated from polymeric materials, but, may include lenses formed from other suitable materials including glass and crystal. FIGS. 23A, 23B and 23C illustrate the geometrical characteristics of lens 84, 86A and 86B, respectively. Lens 86A and 86B may be bonded to each other along adjacent end surfaces and are configured such that an air gap exists between the working portion of the adjacent lens surfaces.

Doublets 86, 86 of lens module 80 may be interconnected by a spacer. In a preferred embodiment, the spacer includes an aperture stop. The aperture stop will determine the diameter of the cone of energy which the system will accept from an axial point on the object. Further, each module 80 in relay portion 64 may be interconnected by spacers to form a single relay lens unit, thereby facilitating mounting of the relay portion within the endoscope.

Referring to FIG. 22D, the geometrical characteristics of lens module 80 are defined by entrance image plane 85A, intermediate surfaces 85B–85M and exit image plane 85N. The geometrical and optical parameters of this module are recorded in Table 6 below.

TABLE 6

| SURFACE | RADIUS | THICKNESS | MEDIUM | INDEX |
|---|---|---|---|---|
| A | Entrance Image Plane | 12.433 | Air | 1.0003 |
| B | −2206.0 | 1.000 | Polycarb. | 1.590081 |
| C | −24.2712 | 29.537 | Air | 1.0003 |
| D | 31.9766 | 1.000 | Acrylic | 1.493795 |
| E | −13.8659 | 0.127 | Air | 1.0003 |
| F | −13.7739 | 1.000 | Styrene | 1.595010 |

TABLE 6-continued

| SURFACE | RADIUS | THICKNESS | MEDIUM | INDEX |
|---|---|---|---|---|
| G | −47.7703 | 16.732 | Air | 1.0003 |
| H | 47.7703 | 1.000 | Styrene | 1.595010 |
| I | 13.7739 | 0.127 | Air | 1.0003 |
| J | 13.8659 | 1.000 | Acrylic | 1.493795 |
| K | −31.9766 | 29.537 | Air | 1.0003 |
| L | 24.2712 | 1.000 | Polycarb. | 1.590081 |
| M | 2206.0 | 12.433 | Air | 1.0003 |
| N | Exit Image Plane | | | | dimensions are in millimeters
Index calculated for wavelength of 546.07 nm

Referring now to FIG. 24, in combination with FIG. 20, the ocular portion of optical system 60 is illustrated in detail. Ocular portion 66 includes doublet 90 having first lens 92 and second lens 94, which are fabricated from polystyrene and an acrylic, respectively. In a preferred embodiment, lens 92 is a meniscus(concavo-convex) lens and lens 94 is a double convex lens. FIGS. 25A and 25B illustrate the geometrical characteristics of lenses 92 and 94, respectively.

A field stop 96 may be provided and preferably positioned at the distal end of the ocular portion as shown in FIG. 24. Field stop 96 functions in limiting the size or angular extent of the object which the system will image.

Referring to FIG. 24, the geometrical characteristics of ocular portion 66 are defined by entrance image plane 95A, surfaces 95B–95E and exit image plane 95F. The geometrical characteristics and optical parameters of the ocular portion are recorded in Table 7 below:

TABLE 7

| SURFACE | RADIUS | THICKNESS | MEDIUM | INDEX |
|---|---|---|---|---|
| A | Entrance Image Plane | 18.527 | Air | 1.0003 |
| B | 15.9322 | 1.000 | Styrene | 1.595010 |
| C | 6.7010 | 0.300 | Air | 1.0003 |
| D | 7.0264 | 3.000 | Acrylic | 1.493795 |
| E | −16.5390 | 19.526 | Air | 1.003 |
| F | Exit Image Plane | | | | dimensions are in millimeters
Index calculated for wavelength of 546.07 nm

The optical system of FIG. 20 effectively transfers a bright image of an object to the viewer. Similar to the embodiment of FIG. 1, lens separations, lens surface powers and focal lengths may be selected to substantially reduce vignetting of light beams at the edge of the view. Thus, substantially all of the light received by the objective lens can be transmitted through the endoscopes without the use of rod lenses.

It is also within the scope of the present invention for the lenses of objective portion 62, relay portion 64 and ocular portion 66 to be fabricated solely from polymeric materials. However, the lenses may be made from other materials including glass and crystal, as well as materials created by SOL-GEL Technology. Further, it is possible to incorporate alternative objective and ocular portions along with the relay portion 64 of FIGS. 22A–D without departing from the principles of the invention. It is also possible to incorporate an illumination system such as the systems previously described in connection with the embodiment of FIG. 1.

To the extent not already indicated, it will be understood by those of ordinary skill in the art that any one of various specific embodiments herein described and illustrated may be further modified to incorporate features shown in other of the specific embodiments.

The invention in its broader aspects therefor is not limited to the specific embodiments herein shown and described but departures may be made therefrom within the scope of the accompanying claims without departing from the principles of the invention and without sacrificing its chief advantages.

What is claimed is:

1. A method for manufacturing and assembling an optical system for a rigid endoscope comprising the steps of:

injecting a liquified polymeric material into a lens mold configuration including a plurality of lens mold compartments and a spine compartment interconnecting the lens mold compartments to form a molded spine having a plurality of aligned molded lenses integrally connected to the molded spine;

transferring the molded spine and molded lenses to a coating process and mounting the molded spine within a coating retainer;

coating the molded lenses with an anti-reflection coating;

removing the molded spine with the molded lenses from the coating retainer and transferring the molded spine and molded lenses to an assembly process;

mounting the molded spine within an assembly retainer; and assembling the molded lenses in an endoscopic tube and detaching the molded spine from the molded lenses.

2. A method for manufacturing and assembling an optical system for a rigid endoscope, comprising the steps of:

providing a lens mold configuration including a plurality of axially aligned lens mold compartments and a spine compartment interconnecting the lens mold compartments;

injecting a liquified polymeric material into the lens mold configuration to form a plurality of molded lenses aligned along an optical axis and a molded spine interconnecting the molded lenses;

transferring the molded spine and connected molded lenses to an assembly process; and assembling the molded lenses in an endoscopic tube and detaching the molded spine from the molded lenses.

3. The method of claim 2 wherein the step of providing includes providing the lens mold configuration having a plurality of identical lens mold compartments.

4. The method of claim 3 wherein the step of injecting includes injecting a liquified polymeric material into the lens mold configuration to form a molded spine having a plurality of identical lenses.

5. The method of claim 2 wherein the step of providing includes providing a lens mold configuration having a plurality of lens mold compartments wherein the lens mold compartments are configured and arranged to form a relay lens module consisting of, in succession, a first single curved lens, a first doublet lens, a second doublet lens and a second curved lens.

6. The method of claim 5 wherein the step of injecting includes injecting the polymeric material into the lens mold configuration to form the molded spine having the relay lens module attached thereto, the relay lens module consisting of, in succession, a first single curved lens, a first doublet lens, a second doublet lens and a second curved lens.

7. The method of claim 2 wherein the step of injecting includes injecting a liquified polymeric material selected from the group consisting of acrylics, polystyrenes, polycarbonates, and styrene-acrylonitrile (SAN) copolymers.

8. The method of claim 2 wherein the step of injecting a liquified polymer is succeeded by a step of coating the lenses attached to the molded spine with an anti-reflection coating.

9. The method of claim 8 wherein the step of coating the lenses includes mounting the molded spine within a coating retainer.

10. The method of claim 2 wherein the step of assembling the lenses includes the step of mounting the molded spine within an assembly retainer.

11. The method of claim 1 wherein the step of injecting includes injecting a liquified polymeric material into the lens mold configuration to form a molded spine having a plurality of aligned molded lenses, each molded lens integrally connected along an outer peripheral surface portion to the molded spine.

12. The method of claim 2 wherein the step of injecting includes injecting a liquified polymeric material into the lens mold configuration to form a molded spine having a plurality of molded lenses, each molded lens integrally connected along an outer peripheral surface portion to the molded spine.

* * * * *